US007222091B2

(12) United States Patent
Yoshida

(10) Patent No.: US 7,222,091 B2
(45) Date of Patent: May 22, 2007

(54) METHOD, SYSTEM AND MEDIUM FOR ORDERING AND MARKETING EYEGLASSES VIA A NETWORK

(75) Inventor: Takehiko Yoshida, Higashiosaka (JP)

(73) Assignee: Vision Optic Co., Ltd., Osaka (JP)

( * ) Notice: Subject to any disclaimer, the term of this patent is extended or adjusted under 35 U.S.C. 154(b) by 513 days.

(21) Appl. No.: 10/432,155

(22) PCT Filed: Nov. 15, 2001

(86) PCT No.: PCT/JP01/09978

§ 371 (c)(1),
(2), (4) Date: May 19, 2003

(87) PCT Pub. No.: WO02/42969

PCT Pub. Date: May 30, 2002

(65) Prior Publication Data

US 2004/0064376 A1    Apr. 1, 2004

(30) Foreign Application Priority Data

Nov. 24, 2000  (JP)  .............................. 2000-357482

(51) Int. Cl.
  *G06F 30/00*   (2006.01)
  *G07F 17/30*   (2006.01)
  *A61B 3/00*    (2006.01)
(52) U.S. Cl. ........................... 705/26; 705/27; 351/246
(58) Field of Classification Search .................. 705/26, 705/27; 351/246
See application file for complete search history.

(56) References Cited

U.S. PATENT DOCUMENTS 5,983,201 A * 11/1999 Fay .............................. 705/27

(Continued)

FOREIGN PATENT DOCUMENTS

JP            09-028682         2/1997

(Continued)

OTHER PUBLICATIONS

Unknown author, "PlanetRx.com Shows Vision By Adding Contact Lenses And Eye Care Products To Product Mix," PR Newswire, New York, Jan. 19, 2000, p. 1.*

(Continued)

*Primary Examiner*—M. A. Fadok
*Assistant Examiner*—Amee A. Shah
(74) *Attorney, Agent, or Firm*—Keating & Bennett, LLP

(57) ABSTRACT

A system and method for remotely ordering and purchasing eyeglasses via a network includes a user interface unit, an eyeglass ordering and marketing service center, and a network that connects therebetween. The system includes an eyeglass frame selection unit for selecting eyeglass frames from among a plurality of eyeglass frames in response to user input, a unit for creating display information concerning eyeglass frames, a unit for testing the vision of the user, and an eyeglass lens selection unit for selecting lenses from among a plurality of eyeglass lenses in response to user input. The system also includes an eyeglass ordering and marketing processor wherein the frame selection unit, the vision test unit, and the lens selection unit performing a vision test in response to the requirements of the user. Appropriate eyeglass frames and eyeglass lenses are determined which best fit the user.

4 Claims, 37 Drawing Sheets

U.S. PATENT DOCUMENTS

| | | | |
|---|---|---|---|
| 6,033,076 A * | 3/2000 | Braeuning et al. | 351/224 |
| 6,386,707 B1 * | 5/2002 | Pellicano | 351/246 |
| 6,533,418 B1 * | 3/2003 | Izumitani et al. | 351/204 |
| 6,543,898 B1 * | 4/2003 | Griffin et al. | 351/243 |
| 6,697,783 B1 * | 2/2004 | Brinkman et al. | 705/3 |
| 6,792,401 B1 * | 9/2004 | Nigro et al. | 703/6 |
| 6,944,327 B1 * | 9/2005 | Soatto | 382/154 |

FOREIGN PATENT DOCUMENTS

| | | |
|---|---|---|
| JP | 10-216087 | 8/1998 |
| JP | 11-120213 | 4/1999 |
| JP | 11-167589 | 6/1999 |
| JP | 11-313799 | 11/1999 |
| JP | 2000-123080 | 4/2000 |
| JP | 2000123080 A * | 4/2000 |

OTHER PUBLICATIONS

Unknown author, "First Insight Announces Spectacle Lens Ordering Via The Internet," PR Newswire, New York, Sep. 15, 2000, p. 1.*

Ketai Business Kenkyu-Kai, "Ketai Business 2001" Softbank Publishing Inc., Sep. 1, 2000, pp. 172-192.

Kabushiki Kaisha Kougakusha, "WebShop Kaiten Manual 2000" Aug. 20, 2000, pp. 12-13.

* cited by examiner

FIG. 4   STEP 2   FOR REGISTERED CLIENT

FIG. 5  STEP 3  FOR NON-REGISTERED CLIENT WITH DOCTOR'S PRESCRIPTION

FIG. 6 STEP 4 FOR NON-REGISTERED CLIENT WITHOUT DOCTOR'S PRESCRIPTION (UNDER 40-45 YEARS OF AGE)

STEP 4' FOR NON-REGISTERED CLIENT WITHOUT DOCTOR'S PRESCRIPTION (OVER 40-45 YEARS OF AGE, HAVING NO SUBJECTIVE SYMPTOM OR NOT REQUESTING READY-MADE PRESBYOPIC EYEGLASSES DESPITE SUBJECTIVE SYMPTOM)

STEP 5 FOR NON-REGISTERED CLIENT WITHOUT DOCTOR'S PRESCRIPTION
(OVER 40-45 YEARS OF AGE AND REQUESTING READY-MADE PRESBYOPIC EYEGLASSES)

FIG. 9

LENS SELECTION REFERENCE
INFORMATION DATABASE

| NAME |
|---|
| CLIENT CODE |
| AGE |
| LEVELS OF MAGNIFICATION |
| LENS FUNCTION — THICKNESS OF LENS / WEIGHT OF LENS / DURABILITY / PREVENTION OF UV LIGHT |
| COLORS |
| BUDGET |
| INTENDED USE |

FIG. 10

LENS DATABASE

| MANUFACTURER'S NAME |
|---|
| MODELS |
| INTENDED USE |
| LENS FUNCTION — THICKNESS OF LENS / WEIGHT OF LENS / DURABILITY / PREVENTION OF UV LIGHT |
| COLORS |
| PRICES |
| LEVELS OF MAGNIFICATION |

FIG. 12

USER INFORMATION DATABASE

| NAME |
|---|
| ADDRESS |
| DATE OF BIRTH |
| PHONE NUMBER |
| CONDITION OF EYES |
| REQUEST CONCERNING EYEGLASSES |
| USER INFORMATION IDENTIFICATION (ID) |
| USER PASSWORD |
| USER CODE |
| FACSIMILE NUMBER |
| E-MAIL ADDRESS |
| URL |
| COMPUTER ENVIRONMENTS |

FIG. 13

REFERENCE DATABASE FOR CARRYING OUT VISION TESTS

| PURPOSE OF USE |
|---|
| AGE |
| PREVIOUS LENS MAGNIFICATION NUMBER |
| VISION WITH LENSES OF PREVIOUS MAGNIFICATION NUMBER |
| BALANCE BETWEEN RIGHT AND LEFT EYES WITH PREVIOUS MAGNIFICATION NUMBER |
| PERIOD OF USE OF PREVIOUS EYEGLASSES |
| TYPE OF CONTACT LENSES (IF USED TOGETHER WITH EYEGLASSES) |
| VISION DESIRED TO BE ATTAINED BY CORRECTION |
| PRESENCE OF DISEASES ASSOCIATED WITH VISION |

FIG. 14

VISION TEST DATABASE

| VISION OF UNCORRECTED EYES |
| CORRECTED VISION |
| PUPIL DISTANCES |
| CORRECTED LEVELS OF MAGNIFICATION FOR DISTANCE |
| CORRECTED LEVELS OF MAGNIFICATION FOR READING |
| DATES OF TEST |
| NAME OF A PERSON WHO DETERMINED LEVEL OF MAGNIFICATION |

FIG. 15

VISION TABLE DATABASE

| LEVEL OF MAGNIFI-CATION | LANDOLT RINGS (8 TYPES, 8 DIRECTIONS) |
|---|---|
| 0.1 | ◯ ...... ◯ |
| 0.2 | ◯ ...... ◯ |
| 0.3 | ◯ ...... ◯ |
| ⋮ | ⋮ |
| 0.9 | ◯ ...... ◯ |
| 1.0 | ◯ ...... ◯ |
| 1.2 | ◯ ...... ◯ |
| 1.5 | ◯ ...... ◯ |
| 2.0 | ◯ ...... ◯ |

NEARSIGHTEDNESS INFORMATION
DATABASE

FARSIGHTEDNESS INFORMATION
DATABASE

ASTIGMATISM INFORMATION
DATABASE

| | | SPH.<br>Spherical level of magnification | CYL.<br>Astigmatism level of magnification | AXIS | PRISM | BASE | P. D<br>Pupil distance |
|---|---|---|---|---|---|---|---|
| Level of magnification for distance | R | Concave 6.0D | Concave 2.5D | 180° | | | 57MM |
| | L | Concave 7.5D | Concave 2.5D | 180° | | | |
| Level of magnification for reading | R | | | | | | |
| | L | | | | | | |

EYEGLASS PRESCRIPTION  Mr. Taro YAMADA  Age: 25

Date  April 20, 1999
Prescription number
Hospital number

FIG. 23

USER INFORMATION DATABASE

| NAME |
|---|
| DATE OF BIRTH |
| ADDRESS |
| PHONE NUMBER |
| CONDITION OF EYES |
| REQUEST CONCERNING EYEGLASSES |
| USER INFORMATION IDENTIFICATION (ID) |
| USER PASSWORD |
| USER CODE |
| FACSIMILE NUMBER |
| E-MAIL ADDRESS |
| URL |
| COMPUTER ENVIRONMENTS |

FIG. 24

DATA INPUT FROM FRAME SELECTION INFORMATION INPUT MEANS

| | | |
|---|---|---|
| SELECTION CRITERIA (IN TEXT DATA) | SENSE OF FASHION | |
| | BUDGET | |
| | FUNCTION | |
| | CONDITION OF FIT TO THE USER'S FACE | |
| FUNCTION 1 (FRONT VIEW OF FACE IMAGE) | 1. DISTANCE BETWEEN RIGHT AND LEFT PUPILS | |
| | 2. WIDTHS FROM CENTER OF RIGHT AND LEFT PUPILS TO FEET OF EARS | |
| | 3. OPENING ANGLES OF TEMPLES DETERMINED BASED ON 2 | |
| FUNCTION 2 (SIDE VIEW OF FACE IMAGE) | 1. DISTANCE FROM FEET OF EARS TO TOPS OF CORNEAS | |
| | 2. BENDING POSITIONS OF TEMPLES | |
| | 3. DISTANCES BETWEEN TOPS OF CORNEAS AND FOOT OF NOSE | |
| | 4. OPENING ANGLES OF PAD BRIDGES DETERMINED BASED ON 3 | |

FIG. 25

FRAME FUNCTIONAL STRUCTURE DATABASE

| SIZE | ACTUAL SIZE (44φ ~ 62φ) | |
|---|---|---|
| FEATURE | SHAPE-MEMORY ALLOY | |
| | SUPER-LIGHT WEIGHT | |
| | SUPER-ELASTICITY | |
| | SIMULTANEOUS FUNCTION AS SUNGLASSES | |
| | PORTABILITY | |
| | OTHERS | |
| FUNCTION 1 (FRONT VIEW OF FACE IMAGE) | 1. DISTANCE BETWEEN RIGHT AND LEFT PUPILS | |
| | 2. WIDTHS FROM CENTER OF RIGHT AND LEFT PUPILS TO FEET OF EARS | |
| | 3. OPENING ANGLES OF TEMPLES DETERMINED BASED ON 2 | |
| FUNCTION 2 (SIDE VIEW OF FACE IMAGE) | 1. DISTANCE FROM FEET OF EARS TO TOPS OF CORNEAS | |
| | 2. BENDING POSITIONS OF TEMPLES | |
| | 3. DISTANCES BETWEEN TOPS OF CORNEAS AND FOOT OF NOSE | |
| | 4. OPENING ANGLES OF PAD BRIDGES DETERMINED BASED ON 3 | |

FIG. 26

FRAME ORNAMENTAL STRUCTURE DATABASE

| | |
|---|---|
| SHAPE | WELLINGTON |
| | LLOYD |
| | OVAL |
| | SQUARE |
| | TONNEAU |
| | BOSTON |
| | BUTTERFLY |
| | AUTO (DROP) |
| MATERIAL | RIMLESS (TWO-POINT, THREE-POINT) |
| | METAL + NYLON RIMMED |
| | CELLULOID + NYLON RIMMED |
| | METAL |
| | CELLULOID |
| | BROW LINE |
| | COMBINATION |
| | OTHERS |
| BRAND | VARIOUS BRANDS |
| COLOR | VARIOUS COLORS |

FIG. 32

<FRONT>   APPLICATION FOR E-CONTACT LENS DELIVERY SERVICE

To: VISION OPTIC CO., LTD.

Customers who have bought contact lenses from Vision Optic Co., Ltd. within the past one year can order the same disposable contact lenses as those currently in use with the e-contact lens delivery service using i-mode. I have read and accepted the "Terms of use of e-contact lens delivery service" on the backside and would like to apply for the service:

1. Name
2. Address
3. Phone number
4. i-mode e-mail address           @
5. ID number        123456
6. Password
7. Registration of places of delivery (Selectable on i-mode)
   1) Home address: same as above
   2) Place of work:
      Company name
      Company address
      Company phone number
   3) Nearby retail shop of Vision Optic Co., Ltd.
8. Registration of payment methods (Changeable to "pay in shop" or "cash on delivery" on i-mode)
   Credit card number
   Credit card type        XX Card, YY Card, ZZ Card, others
   Expiration date
   I accept the terms of agreement on the backside:  Signature:

For company use only:
Vision Contact member's number

<BACK>   Terms of use of "e-contact lens delivery service"

▶ All users of the "e-contact lens delivery service" (hereinafter the Service) must agree to and comply with the terms of use.
● The Service will use the personal information of users given at the time of purchase from Vision Optic Co., Ltd. The registered personal information will not be disclosed to a third party excluding us except when
   1) The registered user has given a prior approval;
   2) Disclosure of the information is ordered by law;
   3) Information is disclosed to a commissioned party that is required to provide the registered user with the Service.
▶ Users are asked to entrust us with the selection of information sent from the Service.
▶ No guarantee is given as to the information and the like available through the use of the Service.
▶ Contents of the Service may change without prior notice.
▶ Service may be subject to interruption or unavailable for brief periods because of problems on our side.
▶ For the safety of your eyes, do not use contact lenses for more than a preset period of time.
▶ In case of a sign of abnormality, stop wearing the contact lenses immediately and seek for medical advice from an ophthalmologist.
▶ Our sales of disposable contact lenses is based on most updated prescription data of the users who have purchased contact lenses from Vision Optic Co., Ltd. within the past one year. Our service does not assume any medical responsibility.
▶ Users who have not visited our shop for more than one year will be denied sales of products.
▶ Regular visits to the ophthalmologist must be paid as instructed even in the absence of any symptom.
▶ After the receipt of an order, no request for cancellation, return, change, or replacement of the ordered item will be accepted.
▶ If the user has selected the option of "pay in shop" or "cash on delivery" and does not pick up the product within three months from the date of order, the ownership of the product will automatically belong to us.
▶ Our contact lenses must not be assigned or sold to a third party.
▶ Any change to prescription data must be made in accordance with an instruction from the ophthalmologist.
▶ Users are responsible for any input error when placing an order by the use of i-mode.

FIG. 35

★TERMS OF AGREEMENT★
1 Return

▼ All users of the "e-contact lens delivery service" (hereinafter the Service) must agree to and comply with the terms of use.
● The Service will use the personal information of users given at the time of purchase from Vision Optic Co., Ltd. The registered personal information will not be disclosed to a third party excluding us except when
1) The registered user has given a prior approval;
2) Disclosure of the information is ordered by law;
3) Information is disclosed to a commissioned party that is required to provide the registered user with the Service.
▼ Users are asked to entrust us with the selection of information sent from the Service.
▼ No guarantee is given as to the information and the like available through the use of the Service.

▼ Contents of the Service may change without prior notice.
▼ Service may be subject to interruption or unavailable for brief periods because of problems on our side.

2 Read next

FIG. 36

★TERMS OF AGREEMENT★

1  Back to previous page

▼ For the safety of your eyes, do not use contact lenses for more than a preset period of time.
▼ In case of a sign of abnormality, stop wearing the contact lenses immediately and seek for medical advice from an ophthalmologist.
▼ Our sales of contact lenses is based on lens prescription data provided by members. Our club does not assume any medical responsibility.
▼ Regular visits to the ophthalmologist must be paid as instructed even in the absence of any symptom.
▼ After the receipt of an order, no request for cancellation, return, change, or replacement of the ordered item will be accepted.
▼ Our contact lenses must not be assigned or sold to a third party.
▼ Any change to prescription data must be made in accordance with an instruction from the ophthalmologist.
▼ Users are responsible for any input error when placing an order by the use of i-mode.

2  Accept
0  Return

FIG. 39

For customers who have not
visited the retail shop for
more than one year:

> ★NOTICE★
>
> Dear Mr/Ms/Mrs AA.
> Our record shows that you have not visited our shop for more than one year. We suggest that you visit an ophthalmologist to test the vision again and have a new prescription.
>
> ○ Return For customers whose credit
card has expired:

> ★NOTICE★
>
> Dear Mr/Ms/Mrs AA.
> The credit card you registered with us for your payment has expired. Please let us know in the following site your new expiration date by e-mail. Once it is confirmed, you can use the card right away:
>
> http://www.info@vision-megane.co.jp
>
> ○ Return

FIG. 40

★REGISTRATION PROCEDURE COMPLETED★
Dear Mr/Ms/Mrs AA,
We keep your contact lens data and are ready to take your order. Please order now.

2 Repeat previous order
0 Return

FIG. 41

Our record shows that you are not a registered member of our service. Please visit a nearby retail shop of Vision Optic Co., Ltd. to register.

FIG. 42

Dear Mr/Ms/Mrs AA,
Please confirm that the following data of the contact lenses that you are now wearing is correct.
▼ NAME: Takehiko Yoshida
▼ DATE OF PURCHASE: January 25, 2000
▼ SHOP OF PURCHASE: Vision Optic Co., Ltd. Umeda Branch
▼ PURCHASED LENS: YYY lens
▼ LENS DATA:
Right eye
Magnification number −3.5
Base curve 8.2
Left eye
Magnification number −3.5
Base curve 8.2
Is this data correct?

1  Yes
2  No

FIG. 43

Please select place of delivery.
Registered places of delivery
1. Home address
4-2, Choeiji-cho, Higashiosaka-shi
Phone number
06-6783-3288
2. Place of work
Yoshida Eye Clinic
1-1-1, Umeda, Kita-ku, Osaka-shi
06-6666-6666
3. Nearby retail shop of Vision Optic Co., Ltd.
Vision Optic Co., Ltd.
Umeda Branch
06-6666-1111

OK    Change

FIG. 44

Please enter your desired delivery address.

NAME

ADDRESS

PHONE NUMBER

Send    Reset

FIG. 45

Selection of lens
to be ordered

Do you wish to order YYY lens?

Yes    No

FIG. 46

Determination of
number of order items

Please enter the number of lenses you wish to order
(up to 12 lenses per each eye).
RIGHT EYE  3
LEFT EYE   3

OK    Reset

FIG. 47

Confirmation of payment method

Do you wish to pay by your pre-registered credit card?

Yes    No

FIG. 48

Please check the order contents.
▼ NUMBER OF ORDERED ITEMS:
Right eye 3
Left eye 3
▼ ORDERED LENS:
YYY lens
▼ LENS DATA:
Right Eye
　Magnification number −3.5
　Base curve 8.2
Left Eye
　Magnification number −3.5
　Base curve 8.2
▼ PLACE OF DELIVERY:
Home address: 4-2, Choeiji-cho, Higashiosaka-shi
▼ ADDRESSEE:
Takehiko Yoshida
▼ PHONE NUMBER:
06-6483-3288
▼ PAYMENT METHOD:
Credit card
▼ PRICE OF PRODUCT:
6,500 yen x 3
Shipping charge: None
Total sum: 19,500 yen ( Order )
( Cancel )

FIG. 49

> Subject:
>
> > Notice from e-contact lens delivery service
>
> Message:
>
> > Dear Mr/Ms/Mrs AA,
> > Thank you for using e-contact lens delivery service. Your order has been received on YY/ZZ and the ordered lenses will be delivered to your home address on AA/BB.
> > ● THE ORDER CONTENTS:
> > ▼ NUMBER OF ORDERED ITEMS:
> > Right eye 3
> > Left eye 3
> > ▼ ORDERED LENS:
> > YYY lens
> > ▼ LENS DATA:
> > Right eye
> >   Magnification
> >   Number −3.5
> >   Base curve 8.2
> > Left eye
> >   Magnification
> >   Number −3.5
> >   Base curve 8.2
> > ▼ PLACE OF DELIVERY:
> > Home address: 4-2, Choeiji-cho, Higashiosaka-shi
> > ▼ ADDRESSEE:
> > Takehiko Yoshida
> > ▼ PHONE NUMBER:
> > 06-6483-3288
> > ▼ PAYMENT METHOD:
> > Cash on delivery
> > ▼ PRICE OF PRODUCT:
> > 6,500 yen x 3
> > Shipping charge: None
> > Total sum: 19,500 yen
> > We look forward to serving your needs again in the future.

FIG. 50

Please enter a correct magnification number. We will send you a message by e-mail once it has been confirmed. Please enter

▼ YOUR NAME

▼ DATE OF PURCHASE

OK

Reset

FIG. 51

Please select the shop of purchase:

1 Tokyo
2 Saitama
3 Chiba
4 Shizuoka
5 Osaka
6 ....

OK

Reset

METHOD, SYSTEM AND MEDIUM FOR ORDERING AND MARKETING EYEGLASSES VIA A NETWORK

BACKGROUND OF THE INVENTION

1. Field of the Invention

The present invention relates to an eyeglass ordering and marketing system and a method therefor in which anyone can place an order for and buy eyeglasses via a network.

2. Description of the Prior Art

Presently, to take a vision test with uncorrected eyes or corrected eyes, one has to visit an ophthalmologist or visit an eyeglass shop to have his or her vision tested with an optometer apparatus located at the office of the ophthalmologist or the eyeglass shop.

Recently, for example, virtual malls are provided on networks, such as the Internet. However, eyeglass shops provided in the virtual malls offer no system for ordering and marketing eyeglasses after confirming the wearing conditions and characteristics of eyeglass frames.

When a customer does not want to spend the time required to visit an eyeglass shop, such a system for remotely ordering and marketing eyeglasses would enable the customer to purchase eyeglasses via the Internet.

When a customer's vision deteriorates such that his or her current eyeglasses or contact lenses are ineffective, he or she has to determine if it is necessary to buy new eyeglasses or contact lenses. Such a system for ordering and marketing eyeglasses which remotely provides a vision test for uncorrected or corrected eyes and which allows one to place an order for and buy eyeglasses based on the resulting test data would be beneficial.

SUMMARY OF THE INVENTION

To overcome the problems described above, preferred embodiments of the present invention provide a system and method which allows customers to place an order for and buy eyeglasses remotely via a network.

A first preferred embodiment of the present invention provides a network-based eyeglass ordering and marketing system including a user interface unit and/or a mobile interface, an eyeglass ordering and marketing service center, and a network connecting therebetween. The system includes a vision testing unit for testing vision of uncorrected eyes, a vision adjusting unit for determining corrected vision by processing data obtained by the vision testing unit, an output unit for transmitting a visual and/or aural instruction regarding lenses, and an input unit for inputting an instruction regarding lenses.

A second preferred embodiment of the present invention provides the network-based eyeglass ordering and marketing system including a user interface unit and/or a mobile interface, an eyeglass ordering and marketing service center, and a network connecting therebetween. The system includes an imaging unit for imaging a user's face and three-dimensionalizing the face image, a frame selection unit for selecting an eyeglass frame chosen by the user, a combining unit for combining an image of the eyeglass frame selected by the frame selection unit with the user's three-dimensional face image data to display a user's eyeglass-wearing image, an output unit for transmitting a visual and/or aural instruction regarding eyeglass frames, and an input unit for inputting an instruction regarding eyeglass frames.

A third preferred embodiment of the present invention is a recording medium having a program of a network-based eyeglass ordering and marketing system recorded thereon, the system including a user interface unit and/or a mobile interface, an eyeglass ordering and marketing service center, and a network connecting therebetween. The system recorded on the recording medium includes a vision testing unit for testing vision of uncorrected eyes, a vision adjusting unit for determining corrected vision by processing data obtained by the vision testing unit, an output unit for transmitting a visual and/or aural instruction regarding lenses, and an input unit for inputting an instruction regarding lenses.

A fourth preferred embodiment of the present invention is a recording medium having a program of a network-based eyeglass ordering and marketing system recorded thereon, the system including a user interface unit and/or a mobile interface, an eyeglass ordering and marketing service center, and a network connecting therebetween. The system recorded on the recording medium includes an imaging unit for imaging a user's face and three-dimensionalizing the face image, a frame selection unit for selecting an eyeglass frame picked up by the user, a combining unit for combining an image of the eyeglass frame selected by the frame selection unit with the user's three-dimensional face image data to display a user's eyeglass-wearing image, an output unit for transmitting a visual and/or aural instruction regarding eyeglass frames, and an input unit for inputting an instruction regarding eyeglass frames.

A fifth preferred embodiment of the present invention is a network-based eyeglass ordering and marketing system including a user interface unit and/or a mobile interface, an eyeglass ordering and marketing service center, and a network connecting therebetween. The system further includes a frame selection unit for selecting an eyeglass frame from among a plurality of eyeglass frames for each user, a creating unit for creating display information chiefly relating to eyeglass frames, a testing unit for testing vision of the user, a lens selection unit for selecting an eyeglass lens from among a plurality of eyeglass lenses for each user, an eyeglass ordering and marketing processing unit for allowing the frame selection unit, the vision testing unit, and the lens selection unit to test vision in response to a requirement of the user sent from the user interface unit and/or the mobile interface, to determine eyeglass frames and lenses suitable for the vision tested by the vision testing unit, for providing the user interface unit and/or the mobile interface with information relating to ordering and marketing, and for concluding an eyeglass purchase contract with the user, and a display information creating unit for creating information relating to eyeglass frames in cooperation with or independently of the frame selection unit and/or the eyeglass ordering and marketing processing unit, and for transmitting the information relating to the eyeglass frames to the user interface unit and/or the mobile interface.

A sixth preferred embodiment of the present invention is a network-based contact lens ordering and marketing system including a user interface unit and/or a mobile interface, a lens ordering and marketing service center, and a network connecting therebetween. The system further includes a contact lens selection unit for selecting a contact lens from among a plurality of contact lenses in accordance with information on each user, a creating unit for creating display information chiefly relating to contact lenses, a lens ordering and marketing processing unit for determining contact lenses in response to a requirement of the user sent from the user interface unit and/or the mobile interface, for providing the user interface unit and/or the mobile interface with information relating to ordering and marketing, and for concluding a contact lens purchase contract with the user, and a display information creating unit for creating information relating to contact lenses in cooperation with or independently of the contact lens selection unit and/or the lens ordering and marketing processing unit, and for transmitting the information relating to the contact lenses to the user interface unit and/or the mobile interface.

A seventh preferred of the present invention is a recording medium having a program of a network-based eyeglass ordering and marketing system recorded thereon, the system including a user interface unit and/or a mobile interface, an eyeglass ordering and marketing service center, and a network connecting therebetween. The system recorded on the recording medium includes a frame selection unit for selecting an eyeglass frame from among a plurality of eyeglass frames for each user, a creating unit for creating display information chiefly relating to eyeglass frames, a testing unit for testing vision of the user, a lens selection unit for selecting an eyeglass lens from among a plurality of eyeglass lenses for each user, an eyeglass ordering and marketing processing unit for allowing the frame selection unit, the vision testing unit, and the lens selection unit to test vision in response to a requirement of the user sent from the user interface unit and/or the mobile interface, to determine eyeglass frames and lenses suitable for the vision tested by the vision testing unit, for providing the user interface unit and/or the mobile interface with information relating to ordering and marketing, and for concluding an eyeglass purchase contract with the user, and a display information creating unit for creating information relating to eyeglass frames in cooperation with or independently of the frame selection unit and/or the eyeglass ordering and marketing processing unit, and for transmitting the information relating to the eyeglass frames to the user interface unit and/or the mobile interface.

An eighth preferred of the present invention is a recording medium having a program of a network-based contact lens ordering and marketing system recorded thereon, the system including a user interface unit and/or a mobile interface, a lens ordering and marketing service center, and a network connecting therebetween. The system recorded on the recording medium includes a contact lens selection unit for selecting a contact lens from among a plurality of contact lenses in accordance with information on each user, a creating unit for creating display information chiefly relating to contact lenses, a lens ordering and marketing processing unit for determining contact lenses in response to a requirement of the user sent from the user interface unit and/or the mobile interface, for providing the user interface unit and/or the mobile interface with information relating to ordering and marketing, and for concluding a contact lens purchase contract with the user, and a display information creating unit for creating information relating to contact lenses in cooperation with or independently of the contact lens selection unit and/or the lens ordering and marketing processing unit, and for transmitting the information relating to the contact lenses to the user interface unit and/or the mobile interface.

A ninth preferred embodiment of the present invention is a method for ordering and marketing eyeglasses via a network using a user interface unit and/or a mobile interface, an eyeglass ordering and marketing service center, and a network connecting therebetween. The method includes the steps of testing vision of uncorrected eyes, adjusting the vision by processing data obtained by the vision test step, outputting a visual and/or aural instruction regarding lenses, and inputting an instruction regarding lenses.

A tenth preferred embodiment of the present invention is a method for ordering and marketing eyeglasses via a network using a user interface unit and/or a mobile interface, an eyeglass ordering and marketing service center, and a network connecting therebetween. The method includes the steps of three-dimensionalizing an imaged user's face for approximating a real face image of the user, selecting an eyeglass frame chosen by the user, combining an image of the selected eyeglass frame with the user's three-dimensional face image to display a user's eyeglass-wearing image, outputting a visual and/or aural instruction regarding eyeglass frames, and inputting an instruction regarding eyeglass frames.

An eleventh preferred embodiment of the present invention is a program for executing a method of ordering and marketing eyeglasses via a network using a user interface unit and/or a mobile interface, an eyeglass ordering and marketing service center, and a network connecting therebetween. The program includes the steps of testing vision of uncorrected eyes, adjusting the vision by processing data obtained by the vision test step, outputting a visual and/or aural instruction regarding lenses, and inputting an instruction regarding lenses.

A twelfth preferred embodiment of the present invention is a program for executing a method of ordering and marketing eyeglasses via a network using a user interface unit and/or a mobile interface, an eyeglass ordering and marketing service center, and a network connecting therebetween. The program includes the steps of three-dimensionalizing an imaged user's face for approximating a real face image of the user, selecting an eyeglass frame chosen by the user, combining an image of the selected eyeglass frame with the user's three-dimensional face image to display a user's eyeglass-wearing image, outputting a visual and/or aural instruction regarding eyeglass frames, and inputting an instruction regarding eyeglass frames.

A thirteenth preferred embodiment of the present invention is a method for ordering and marketing eyeglasses via a network using a user interface unit and/or a mobile interface, an eyeglass ordering and marketing service center, and a network connecting therebetween. The method includes the steps of selecting an eyeglass frame from among a plurality of eyeglass frames for each user, creating display information chiefly relating to eyeglass frames, testing vision of the user, selecting an eyeglass lens from among a plurality of eyeglass lenses for each user, processing eyeglass ordering and marketing made based on the eyeglass frame selection step, the vision test step, and the lens selection step such that vision is tested in response to a requirement of the user sent from the user interface unit and/or mobile interface, determining eyeglass frames and lenses suitable for the vision, providing the user interface unit and/or the mobile interface with information relating to ordering and marketing, and concluding an eyeglass purchase contract with the user, and creating display information relating to eyeglass frames in cooperation with or independently of the frame selection step and/or the eyeglass ordering and marketing processing step, and for transmitting the information on the eyeglass frames to the user interface unit and/or the mobile interface.

A fourteenth preferred of the present invention is a method for ordering and marketing contact lenses via a network using a user interface unit and/or a mobile interface, a lens ordering and marketing service center, and a network connecting therebetween. The method includes the steps of selecting a contact lens from among a plurality of contact lenses for each user, creating display information chiefly relating to contact lenses, processing contact lens ordering and marketing, including determining the contact lens selected in the contact lens selection step in response to a requirement of the user sent from the user interface unit and/or the mobile interface, providing the user interface unit and/or the mobile interface with information relating to ordering and marketing, and concluding a contact lens purchase contract with the user, and creating display information relating to contact lenses in cooperation with or independently of the contact lenses selection step and/or the contact lens ordering and marketing processing step, and for transmitting the information on the contact lenses to the user interface unit and/or the mobile interface.

A fifteenth preferred embodiment of the present invention is a program for executing a method of ordering and marketing eyeglasses via a network using a user interface unit and/or a mobile interface, an eyeglass ordering and marketing service center, and a network connecting therebetween. The program includes the steps of selecting an eyeglass frame from among a plurality of eyeglass frames for each user, creating display information chiefly relating to eyeglass frames, testing vision of the user, selecting an eyeglass lens from among a plurality of eyeglass lenses for each user, processing eyeglass ordering and marketing made based on the eyeglass frame selection step, the vision test step, and the lens selection step such that vision is tested in response to a requirement of the user sent from the user interface unit and/or mobile interface, determining eyeglass frames and lenses suitable for the vision, providing the user interface unit and/or the mobile interface with information relating to ordering and marketing, and concluding an eyeglass purchase contract with the user, and creating display information relating to eyeglass frames in cooperation with or independently of the frame selection step and/or the eyeglass ordering and marketing processing step, and for transmitting the information on the eyeglass frames to the user interface unit and/or the mobile interface.

A sixteenth preferred embodiment of the present invention is program for executing a method of ordering and marketing contact lenses via a network using a user interface unit and/or a mobile interface, a lens ordering and marketing service center, and a network connecting therebetween. The program includes the steps of selecting a contact lens from among a plurality of contact lenses for each user, creating display information chiefly relating to contact lenses, processing contact lens ordering and marketing, including determining the contact lens selected in the contact lens selection step in response to a requirement of the user sent from the user interface unit and/or the mobile interface, providing the user interface unit and/or the mobile interface with information relating to ordering and marketing, and concluding a contact lens purchase contract with the user, and creating display information relating to contact lenses in cooperation with or independently of the contact lenses selection step and/or the contact lens ordering and marketing processing step, and for transmitting the information on the contact lenses to the user interface unit and/or the mobile interface.

The above and other elements, characteristics, features, steps and advantages of the present invention will be apparent from the following detailed description of preferred embodiments of the present invention with reference to the accompanying drawings.

BRIEF DESCRIPTION OF THE DRAWINGS

FIG. 9 is a view illustrating a lens selection reference database.

FIG. 10 is a view illustrating a lens database.

FIG. 12 is a view illustrating an exemplary configuration of a database including user information which is controlled by a database controller at a service center.

FIG. 13 is a view illustrating an exemplary configuration of a database including reference information for vision tests which is controlled by a database controller at a service center.

FIG. 14 is a view illustrating an exemplary configuration of a database including vision test information which is controlled by a database controller at a service center.

FIG. 15 is a view illustrating an exemplary configuration of a database including a vision test table which is controlled by a database controller at a service center.

FIG. 23 is a view illustrating an exemplary configuration of a database including user information which is controlled by a database controller at a service center.

FIG. 24 is a view illustrating an example of data which is input by a frame selection information input unit at a service center.

FIG. 25 is a view illustrating an exemplary configuration of a database on the frame functional structure of each frame which is controlled by a database controller at a service center.

FIG. 26 is a view illustrating an exemplary configuration of a database including the frame ornamental structure of each frame which is controlled by a database controller at a service center.

FIG. 32 is a diagrammatic view illustrating an application form for a contact lens delivery service.

FIG. 35 is a diagrammatic view illustrating a first screen displaying "terms of agreement."

FIG. 36 is a diagrammatic view illustrating a second screen displaying "terms of agreement."

FIG. 39 is a diagrammatic view illustrating screens displaying "notice" which are transmitted to a user who has not visited a shop for more than one year.

FIG. 40 is a diagrammatic view illustrating a screen showing a completion of registration procedure.

FIG. 41 is a diagrammatic view illustrating a screen to be transmitted to a user who is not a registered member of the service.

FIG. 42 is a diagrammatic view illustrating a confirmation of conditions screen.

FIG. 43 is a diagrammatic view illustrating a confirmation of delivery location screen.

FIG. 44 is a diagrammatic view illustrating a screen for inputting a delivery location other than the registered one.

FIG. 45 is a diagrammatic view illustrating a screen displaying "selection of lens to be ordered."

FIG. 46 is a diagrammatic view illustrating a screen displaying "determination of number of order items."

FIG. 47 is a diagrammatic view illustrating a screen displaying "confirmation of payment method."

FIG. 48 is a diagrammatic view illustrating a screen for confirming a price for an order and order contents.

FIG. 49 is a diagrammatic view illustrating a screen informing a delivery date and delivery contents which is transmitted to a user after placing an order.

FIG. 50 is a diagrammatic view illustrating a screen for prompting a user to input correct specifications of a contact lens to be ordered.

FIG. 51 is a diagrammatic view illustrating a first screen for selecting a shop of purchase.

DETAILED DESCRIPTION OF PREFERRED EMBODIMENTS

Figure 1:
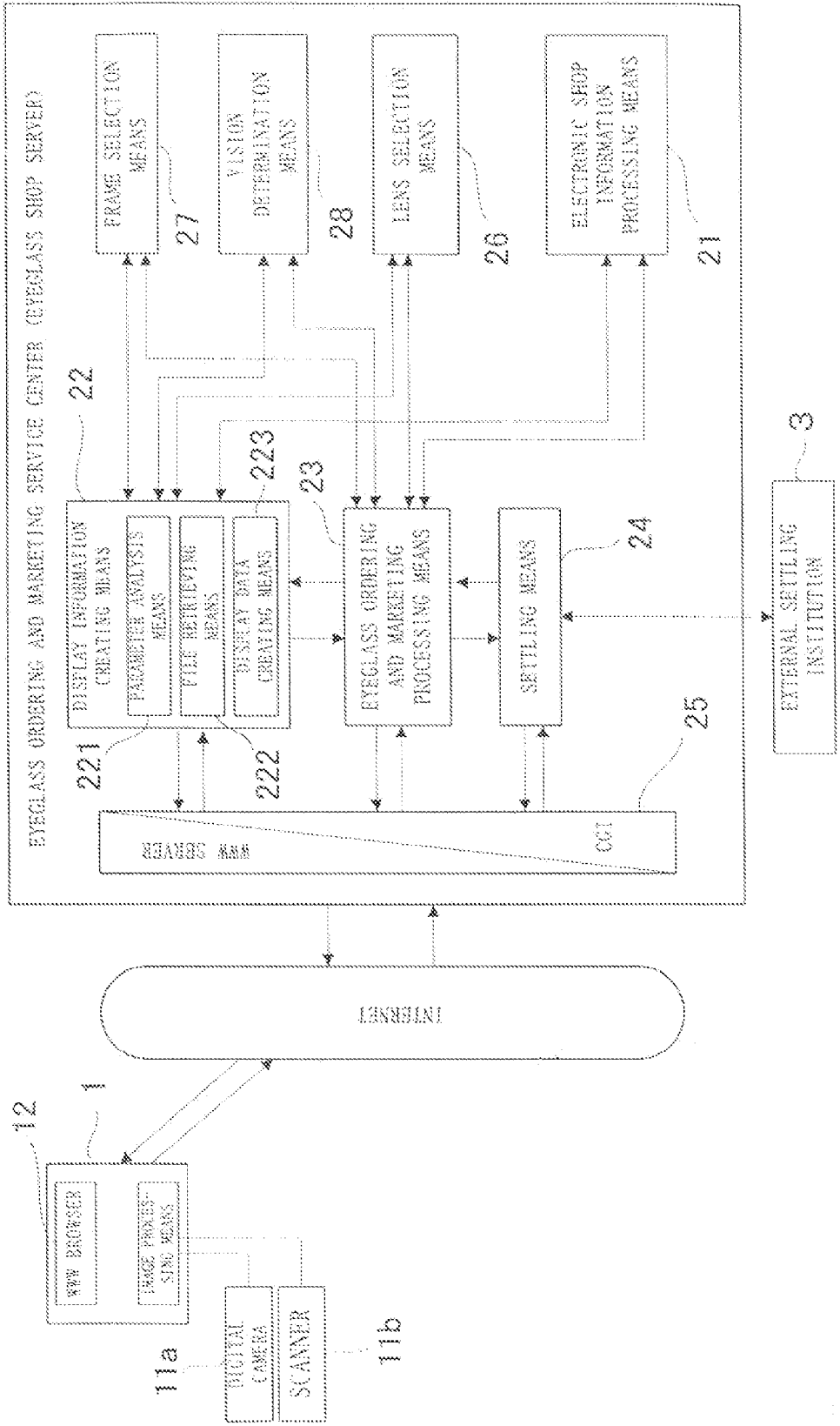
FIG. 1 is a view illustrating an exemplary configuration of a network eyeglass ordering and marketing system according to a preferred embodiment of the present invention.

FIG. 1 is a view illustrating an exemplary configuration of a network eyeglass ordering and marketing system according to a preferred embodiment of the present invention.

As shown in FIG. 1, the network eyeglass ordering and marketing system includes a user interface unit 1 and an eyeglass ordering and marketing service center 2. These components are physically connected to each another via a network.

In the following description the Internet is preferably used to connect the user interface unit 1 to the eyeglass ordering and marketing service center 2.

The network eyeglass ordering and marketing system is provided to market custom-made eyeglasses according to specifications of purchasers, including the eyeglass ordering and marketing service center 2.

The electronic eyeglass ordering and marketing system includes the user interface unit 1, the eyeglass ordering and marketing service center 2, and an external settling institution 3. These components are physically connected to each other via a network.

The user interface unit 1 includes a terminal, such as a personal computer, used by purchasers to place an order for and to obtain their eyeglasses via a network. The user interface unit 1 includes an I/O unit 11 or an interface between a user and the eyeglass ordering and marketing service center 2. More specifically, the user interface unit 1 includes input devices such as a keyboard or a mouse and output devices such as a CRT display.

A keyboard is preferably used as an input device for inputting information such as text data. However, various types of input devices may be used, for example, pointing devices such as a mouse, a track ball, or a joystick, touch panels, or switches and any other suitable data input device.

Furthermore, a digital camera 11a is preferably provided as an image information input device. However, any device, such as a television camera, a video camera, or a digital still camera may be used as long as it allows image information to be digitized for input. In addition, a hard drive and CD-ROM drive are provided as storage units for storing images or other information and enabling image information, programs or other suitable information stored on CD-ROMs to be used. Other devices for storage media such as DVDs, MOs, or memory units may also be used.

In addition, the personal computer according to this preferred embodiment is connected to a computer network (network) or the Internet, such that image information, software, or any other information or data can be transmitted and received via the network.

Moreover, the user interface unit 1 preferably includes a WWW browser 12 as an interface to the server of the eyeglass ordering and marketing service center 2. When the user interface unit 1 includes a personal computer, the WWW browser 12 is a program stored in the memory of the personal computer.

The eyeglass ordering and marketing service center 2 includes an electronic shop information processor 21, a display information creating unit 22, an eyeglass ordering and marketing processor 23, a settling unit 24, and a WWW server/CGI 25.

Specifically, the eyeglass ordering and marketing service center 2 includes information processing devices such as personal computers, workstations, and a server. The electronic shop information processor 21 is stored in a storage unit, such as a magnetic or optical disk unit of the information processing devices. In practice, each of the processors mentioned above, i.e., the WWW server/CGI 25, the display information creating unit 22, the eyeglass ordering and marketing processor 23, and the settling unit 24 is stored in a program format in the memory of the information processing device.

The electronic shop information processor 21 defines product data such as eyeglass lenses and frames, which are provided in the eyeglass ordering and marketing service center 2, in a product definition division via an I/O unit. The product data are stored in a product database as product data information.

In this preferred embodiment, the product data information includes the shelves on which products, such as frames, are exhibited, product numbers, product names, prices, product descriptions of eyeglass lenses, frames, and other relevant and suitable information. The product data information further includes text data, such as product control information, and image data of products, such as frames. The eyeglass ordering and marketing service center 2 also preferably includes an I/O unit which defines an interface to creators of electronic catalogs. The I/O unit accepts the input of product information including text data such as product shelves, product items, and prices, which are required for product definition, or image data showing product shapes, from the creators of the catalogs. The eyeglass ordering and marketing service center 2 also outputs order information on products purchased by purchasers including product information such as product numbers or quantities, information on addressees of products, and payment information such as names of external settling institutions, payment dates, or the amount of payment. The eyeglass ordering and marketing service center 2 may also include an information-processing device such as a personal computer including I/O devices such as a keyboard, a mouse, a CRT display or any other data input device. In this case, the product definition division is defined by a execution program stored in the memory of the information-processing device.

The electronic shop information processor 21 is provided with an electronic open shop information unit that includes a shop database, a product database, and a basket database. The shop database stores information for opening electronic shops and information for defining shop layouts to display product information. The product database stores product data information that has been defined. On the other hand, the basket database accumulates the product information of the product that the user interface unit 1 has been instructed to purchase. The electronic shop information processor 21 performs the function of storing transferred product data information into the product database.

The display information creating unit 22 creates display information such as electronic catalogs in response to a request from the user interface unit 1. The display information creating unit 22 includes a parameter analysis unit 221, a file retrieving unit 222, and a display data creating unit 223. The parameter analysis unit 221 analyzes vision test data, frame selection information, and other useful information, which are received from the user interface unit 1 via the WWW server/CGI 25, and extracts parameters included therein. Based on the parameters extracted by the parameter analysis unit 221, the file retrieving unit 222 retrieves data that has been registered and stored in each database by the electronic shop information processing unit 21. The display data creating unit 223 creates display data that is displayed as WWW pages, based on the data retrieved by the file retrieving unit 222. Thus, the display data creating unit 223 functions as the so-called WWW page creator.

When a product to be purchased (such as an eyeglass lens or a frame) is selected via the user interface unit 1, the eyeglass ordering and marketing processor 23 receives a user ID and a product ID to be purchased from the display information creating unit 22. Based on this information, the eyeglass ordering and marketing processing unit 23 then obtains detailed information about the product to be purchased from the product database, and stores the product information in a user basket database corresponding to the user within the basket database. Subsequently, the eyeglass ordering and marketing processing unit 23 obtains a list of products to be purchased by the purchaser from the basket database, and then passes the list to the display information creating unit 22.

When the user interface unit 1 has decided to purchase a product, the settling unit 24 receives the user ID from the display information creating unit 22 to retrieve product data information corresponding to the purchaser from the basket database. Then, based on the product information that has been retrieved, the settling unit 24 makes a request of the external settling institution 3 for settling processing. The settling unit 24 is informed of the completion of the settling processing by the external settling institution 3, and thereafter notifies the eyeglass ordering and marketing processor 23 and the electronic shop information processor 21 that an order acceptance processing has been completed. In order to notify the user interface unit 1 of the purchase processing, the settling unit 24 also prepares invoice data and sends the invoice data to the display information creating unit 22.

The WWW server (World Wide Web)/CGI (Common Gateway Interface) 25 defines an interface to the user interface unit 1 to receive display request information from the user interface unit 1 as well as transfer display data to the user interface unit 1.

Based on the request sent from the settling unit 24 of the eyeglass ordering and marketing service center 2, the external settling institution 3 performs a settling processing task for payment of the ordered eyeglass.

In addition, the outline of the operation of the user interface unit 1 and the eyeglass ordering and marketing service center 2 will be described below.

In the eyeglass ordering and marketing service center 2, the WWW server/CGI 25 receives eyeglass ordering page information that is sent from the user interface unit 1, and then activates the display information creating unit 22.

The display information creating unit 22 is activated to receive the eyeglass ordering page information from the WWW server/CGI 25, which then enables the parameter analysis unit 221 to analyze the information. The parameter analysis unit 221 outputs information as analytical results such as a shop ID for identifying an electronic shop to be displayed, a catalog template for determining the type of background image for an electronic catalog, the product ID of a product to be displayed, and a user ID for identifying the purchaser. Based on the data output from the parameter analysis unit 221, the file retrieving unit 222 retrieves data in the shop database, product database, and basket database which is necessary to create a display window of a homepage requested by the user interface unit 1.

After the file retrieving unit 222 has retrieved the data, the process is transferred to the display data creating unit 223. The display data creating unit 223 first identifies the type of request from the user interface unit 1. When the request from the user interface unit 1 is one other than "the determination of a product to be purchased" and "the purchase of a product", the display data creating unit 223 creates display data using the result retrieved by the file retrieving unit 222.

When the type of request from the user interface unit 1 is identified as "the determination of a product to be purchased" in the step of identifying the type of a request from the user interface unit 1, that is, when the user has provided an instruction of "putting a selected product into a shopping basket" which reserves a product being displayed, the display data creating unit 223 activates the eyeglass ordering and marketing processor 23.

The eyeglass ordering and marketing processor 23 is activated to receive a user ID and the product ID of the product to be purchased from the display data creating unit 223. With this product ID as key information, the eyeglass ordering and marketing processor 23 receives detailed product data information about the corresponding product from the product database. Then, the product data information retrieved in the foregoing step is stored in the user basket database of the user. The user is identified by the user ID received from the display data creating unit 223. At this point, when no corresponding user basket database exists, a user basket database that corresponds to the user ID is created to store the product data information therein. Then, all pieces of the product data information of the products that the user has selected are retrieved from the user basket database and passed to the display data creating unit 223. In this case, the display data creating unit 223 creates a list of display information of the products that the user intends to purchase, based on the product data information received from the eyeglass ordering and marketing processor 23, and then sends the list of display information to the user interface unit 1. Based on the information displayed at this point, the user can check the products to be purchased or cancel part of or all the products to be purchased.

When the type of request from the user interface unit 1 has been identified as "the purchase of a product" in the step of identifying the type of request from the user interface unit 1, that is, when the user has provided an instruction of his or her decision concerning the purchase of the products that the user has selected so far, the display data creating unit 223 activates the settling unit 24 prior to the creation of display data.

The settling unit 24 is activated to receive a user ID from the display data creating unit 223. With the received user ID, the settling unit 24 retrieves the product data information of the purchased product in the user basket database of the user identified with the user ID in the basket database. Based on the resulting product data information, a request for settling processing is sent to the external settling institution 3. In response to the request, the external settling institution 3 performs a settling processing task, and then notifies the eyeglass ordering and marketing service center 2 of the completion of the settling processing when completed. Since the settling processing performed in the external settling institution 3 is conventional, no detailed description is provided for the settling processing herein.

Upon receipt of a notification from the external settling institution 3 that the settling processing has been completed, the settling unit 24 forwards the information of the order received to the eyeglass ordering and marketing service center 2. The received order information includes information about the ordered product such as the product number and quantity of the product, information about the destination of the product, and the settling information, such as the name of the external settling institution 3 and the date and amount of payment. In the eyeglass ordering and marketing service center 2, the information about the order received from the WWW server/CGI via an I/O unit is displayed. Then, the settling unit 24 creates invoice data for notification of the completion of the settling processing and transmits the invoice data to the display data creating unit 223. The display data creating unit 223 uses the invoice data that has been received to create a display window for notification of the completion of the settling processing, and thus, forwards the window to the user interface unit 1.

The method for ordering and marketing eyeglasses by using a network eyeglass ordering and marketing system will now be described below.

Figure 2:
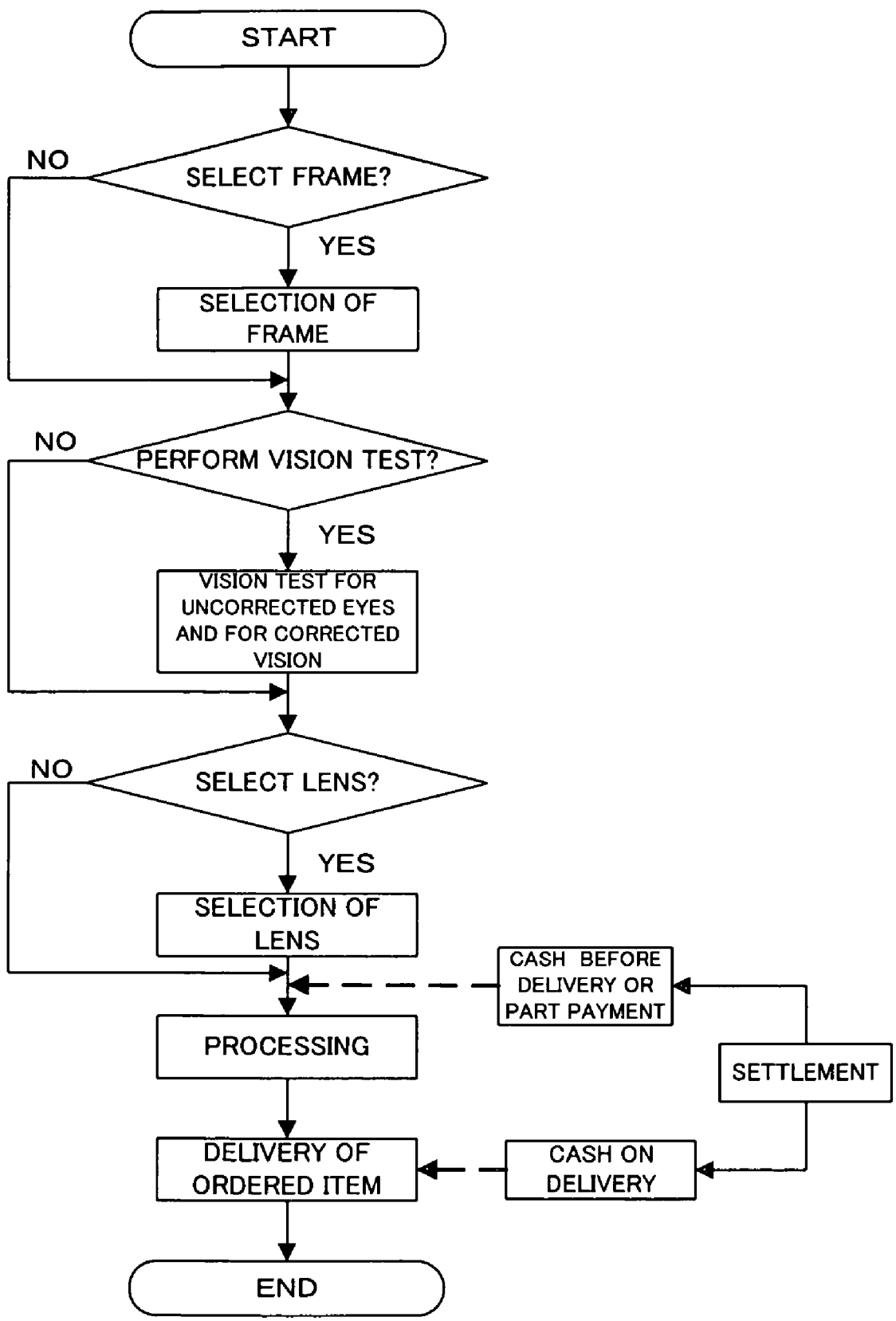
FIG. 2 is a view illustrating a first outline of the process flow of a network eyeglass ordering and marketing system.
Figure 3:
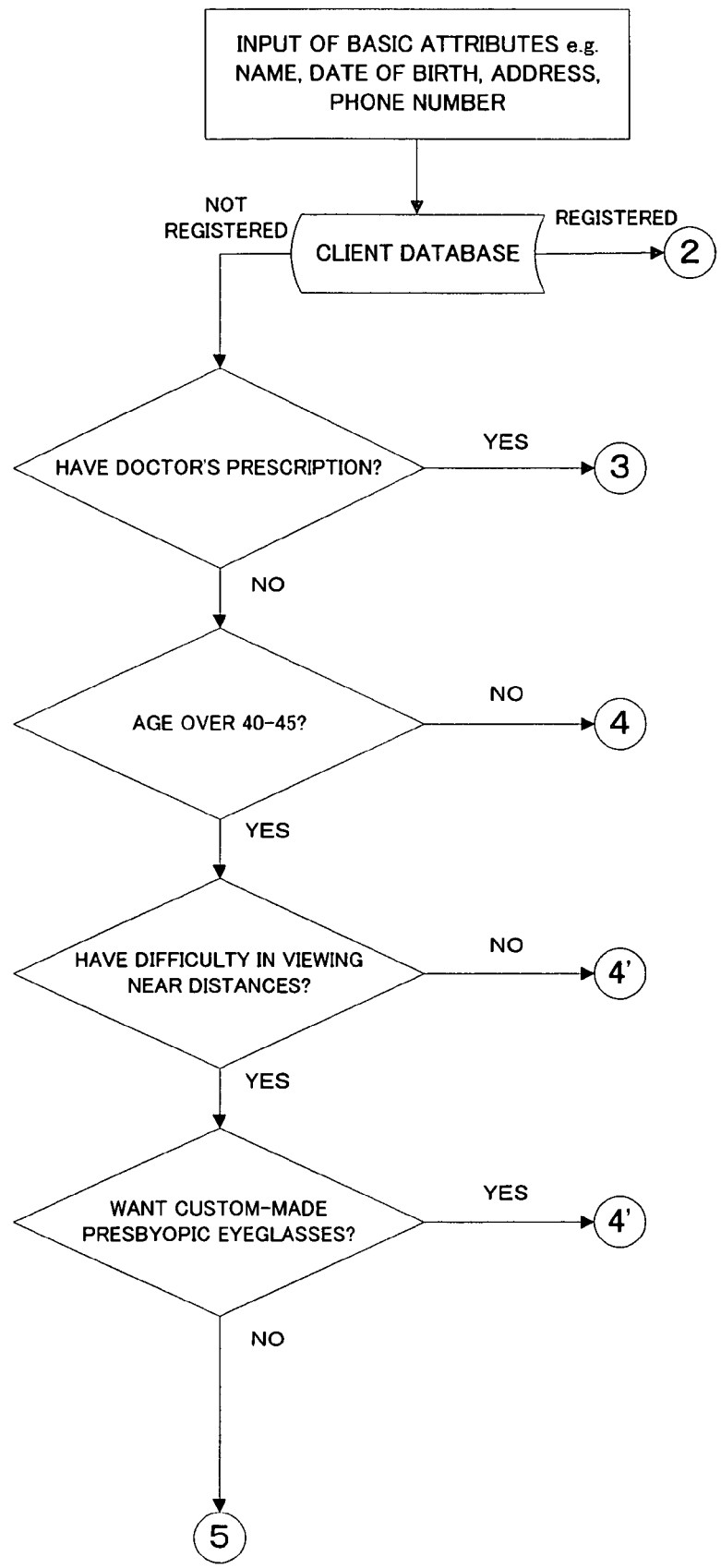
FIG. 3 is a view illustrating a second outline of the process flow of a network eyeglass ordering and marketing system.
Figure 4:
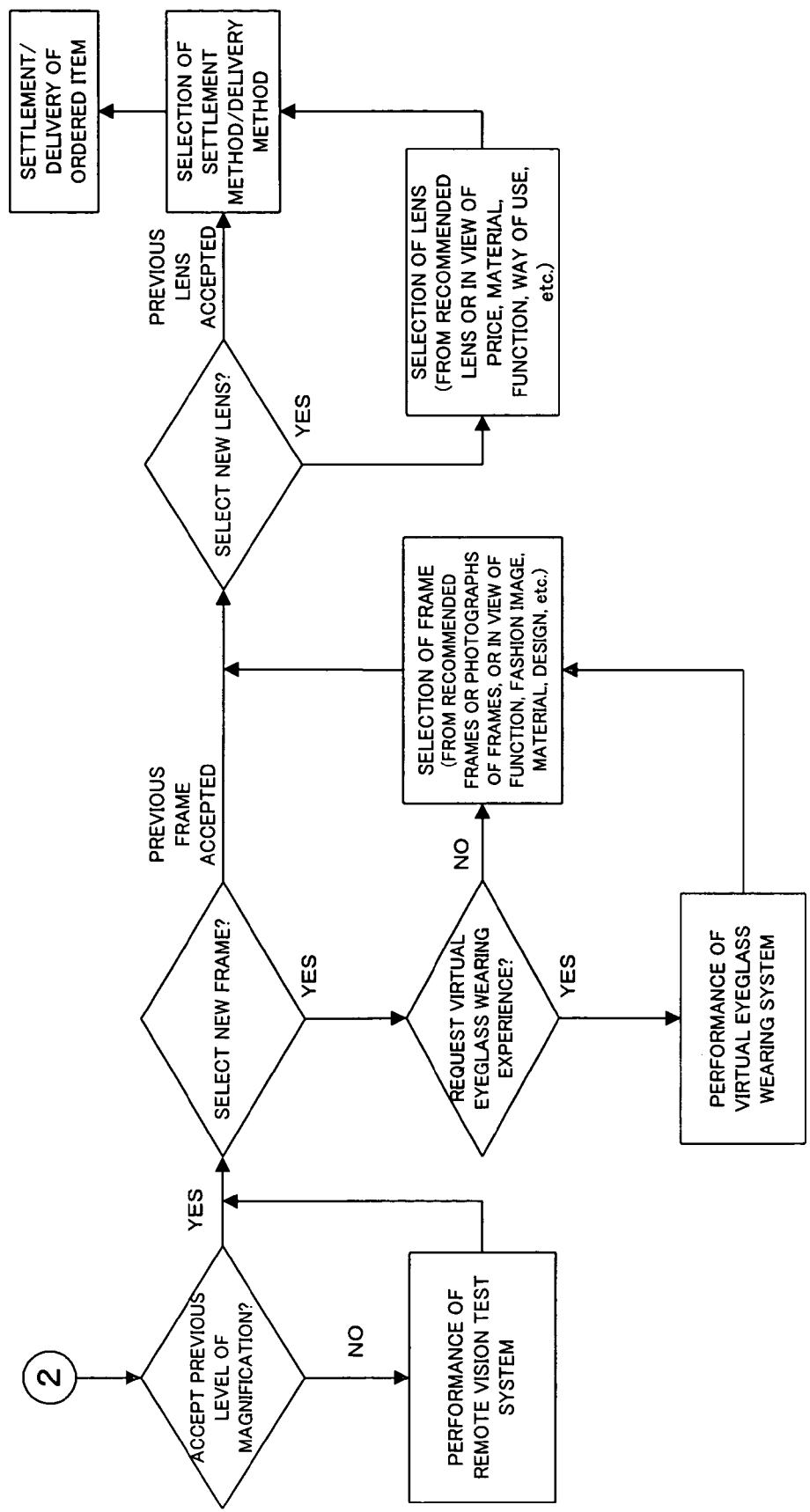
FIG. 4 is a view illustrating an outline of the process flow (step 2) of a network eyeglass ordering and marketing system for existing users.
Figure 5:
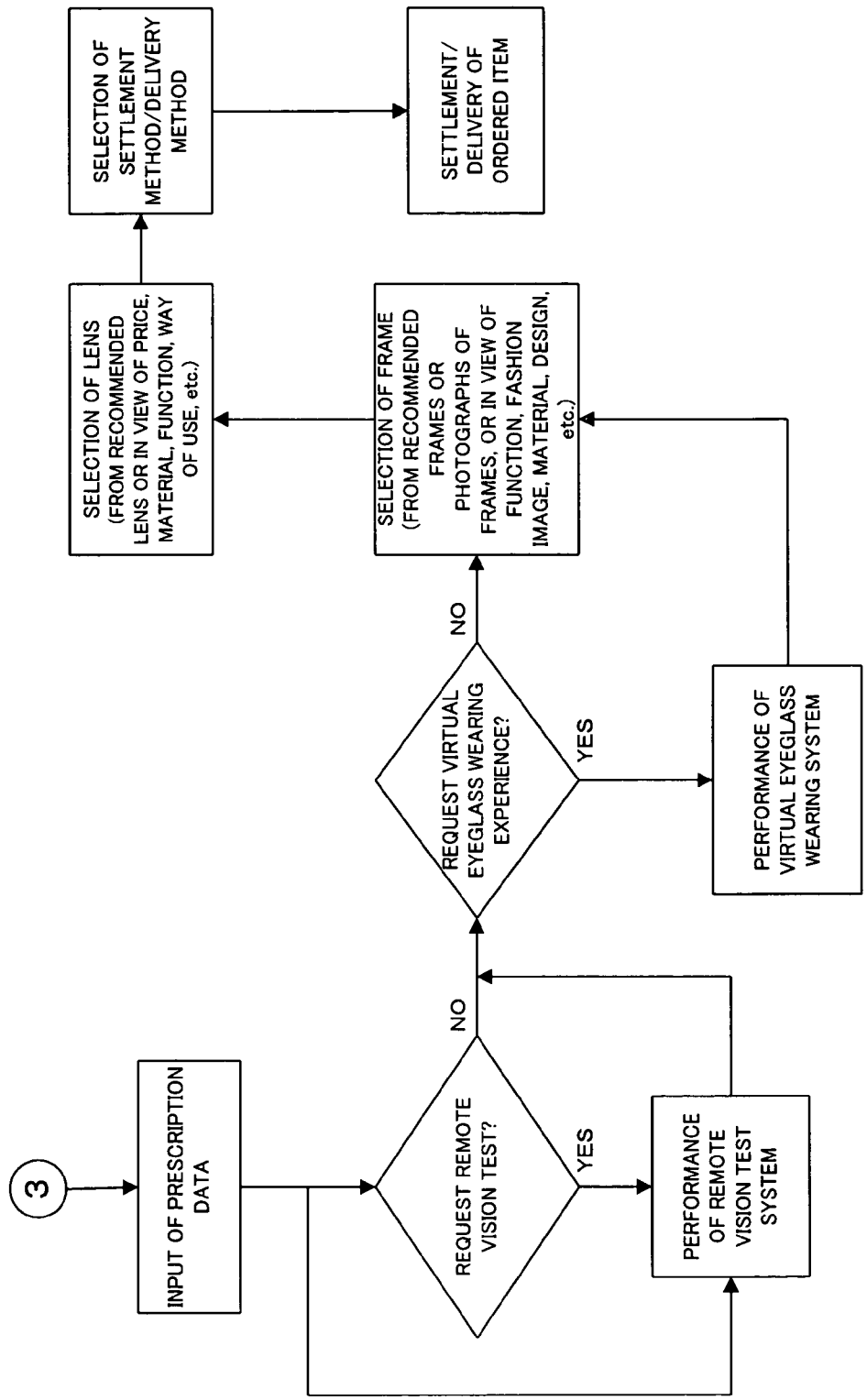
FIG. 5 is a view illustrating an outline of the process flow (step 3) of a network eyeglass ordering and marketing system for unregistered users with a doctor's prescription.
Figure 6:
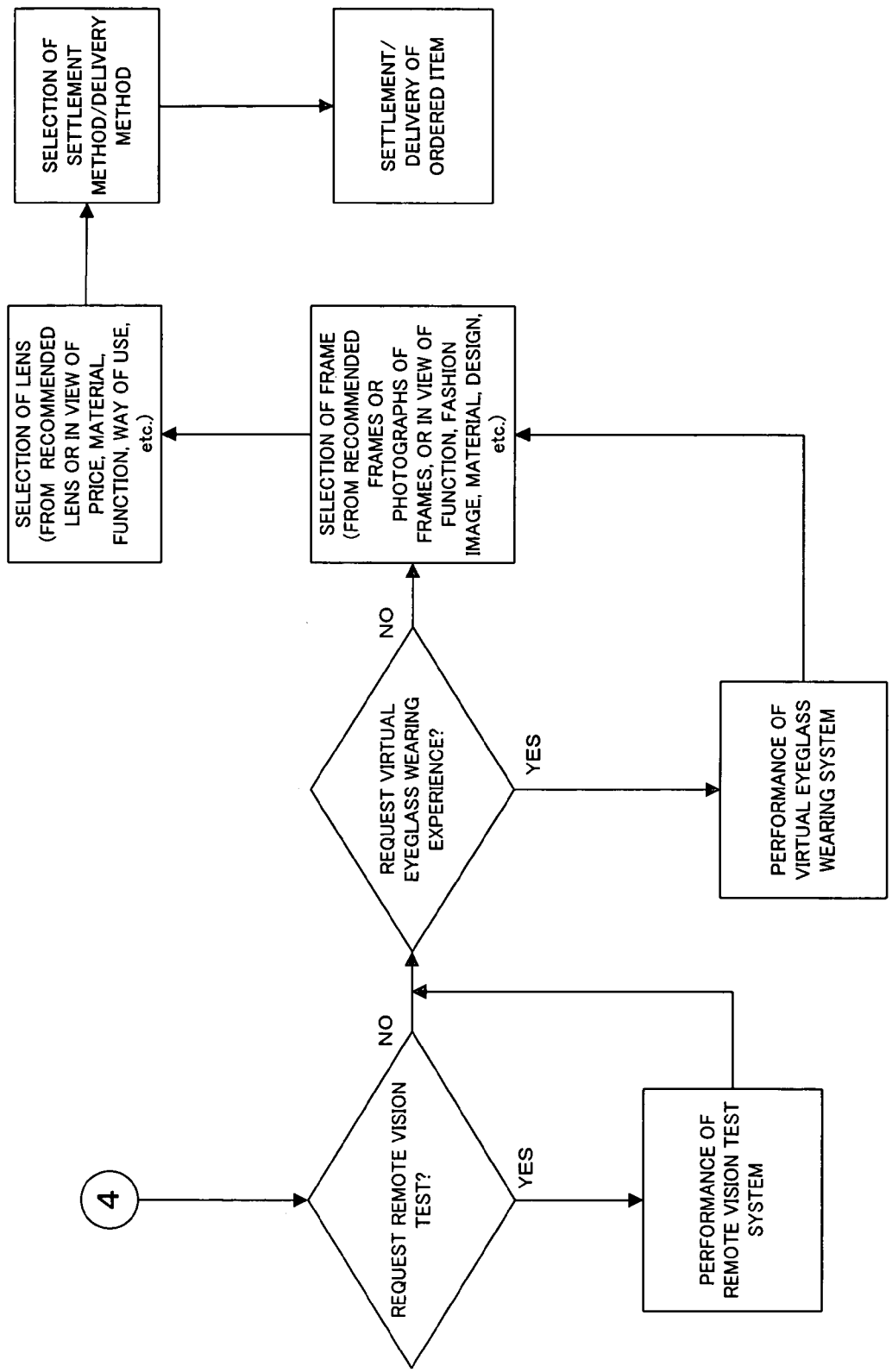
FIG. 6 is a view illustrating an outline of the process flow (step 4) of a network eyeglass ordering and marketing system for unregistered users without a doctor's prescription.
Figure 7:
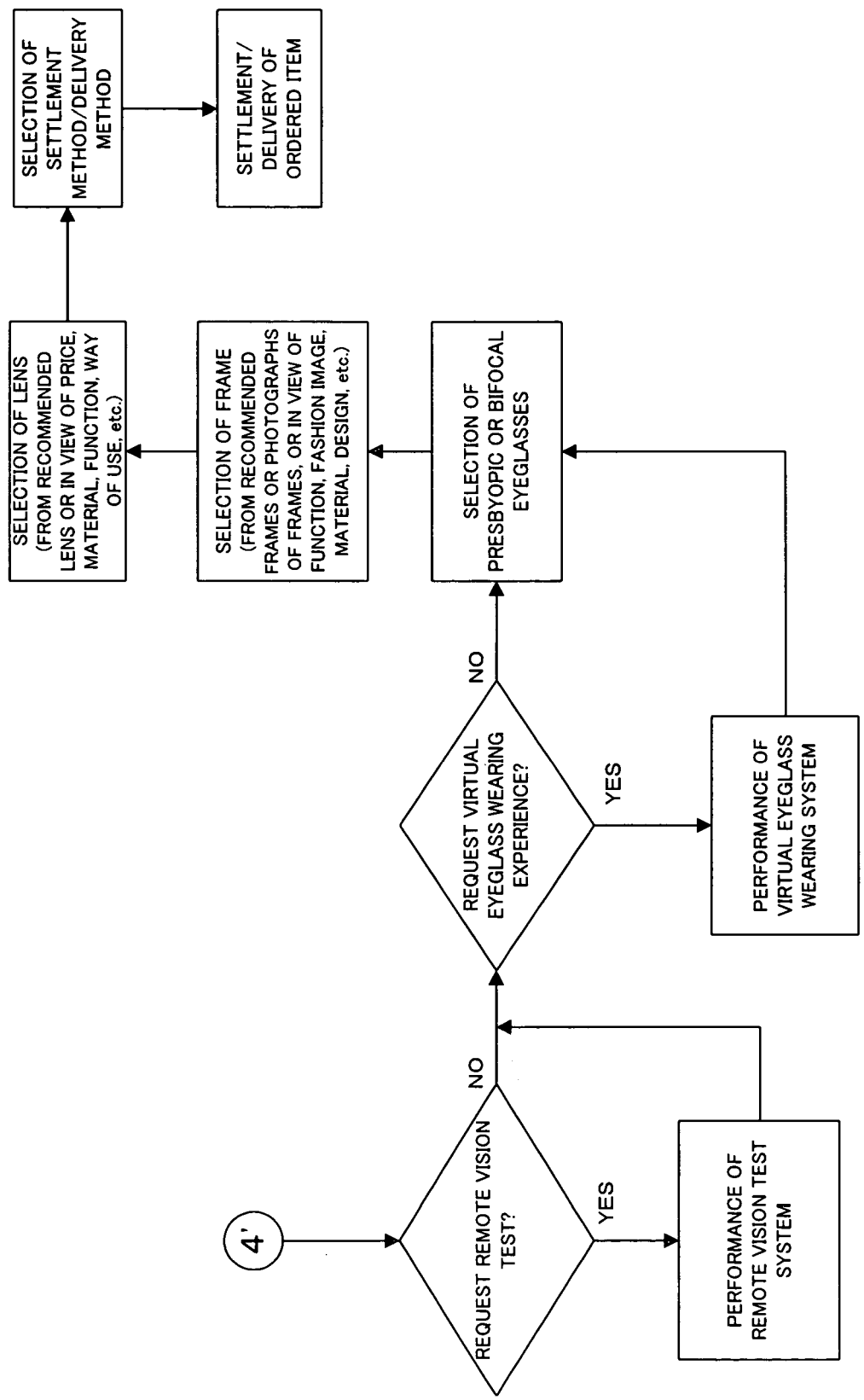
FIG. 7 is a view illustrating an outline of the process flow (step 4') of a network eyeglass ordering and marketing system for unregistered users without a doctor's prescription.
Figure 8:
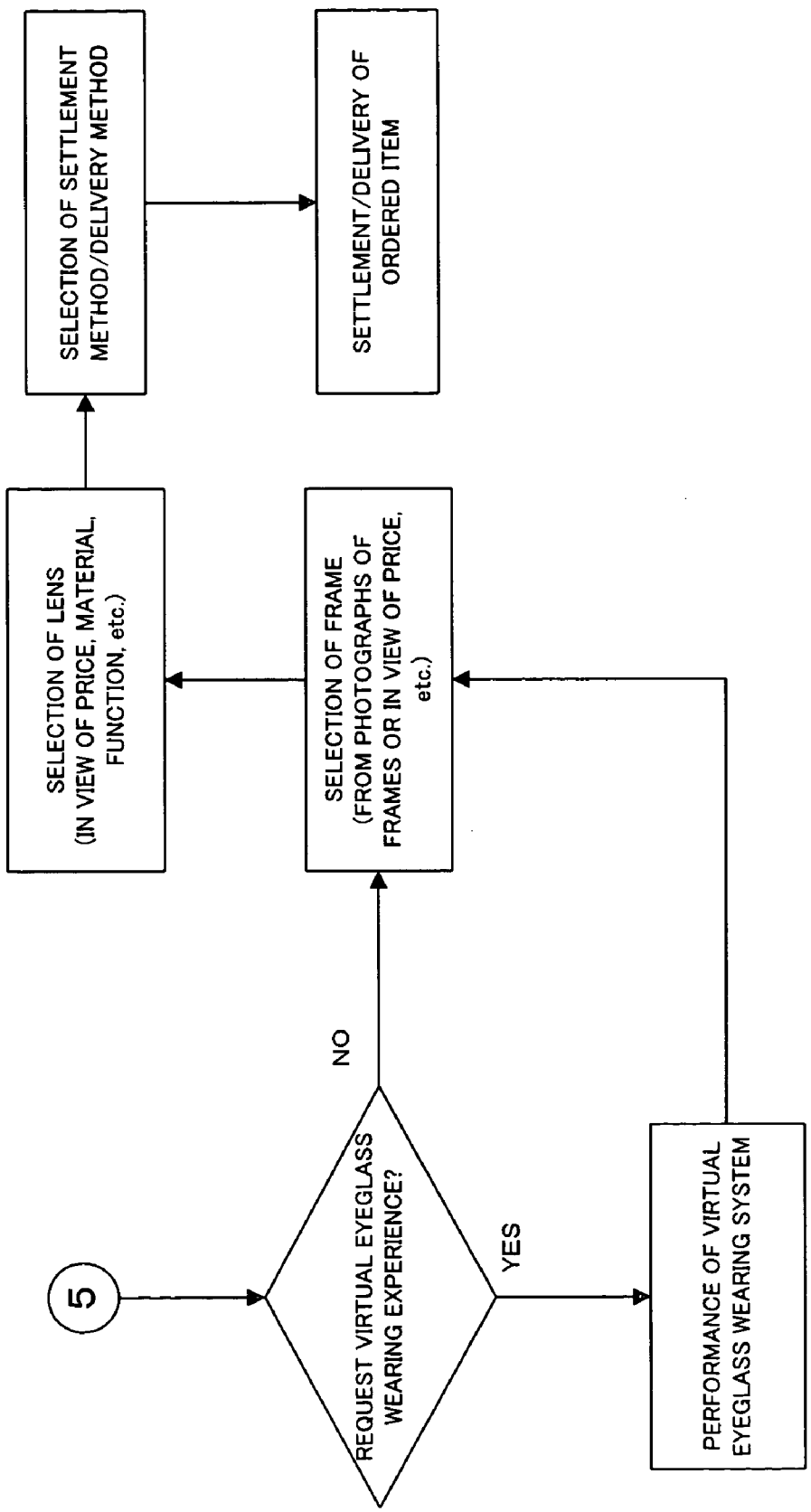
FIG. 8 is a view illustrating an outline of the process flow (step 5) of a network eyeglass ordering and marketing system for selecting ready-made presbyopic eyeglasses.

FIG. 2 is a view illustrating a (first) outline of the process flow of a network eyeglass ordering and marketing system. FIG. 3 is a view illustrating a (second) outline of the process flow of a network eyeglass ordering and marketing system. FIG. 4 is a view illustrating an outline of the process flow (step 2) of a network eyeglass ordering and marketing system for existing users. FIG. 5 is a view illustrating an outline of the process flow (step 3) of a network eyeglass ordering and marketing system for unregistered users with a doctor's prescription. FIG. 6 is a view illustrating an outline of the process flow (step 4) of a network eyeglass ordering and marketing system for unregistered users without a doctor's prescription. FIG. 7 is a view illustrating an outline of the process flow (step 4') of a network eyeglass ordering and marketing system for unregistered users without a doctor's prescription. FIG. 8 is a view illustrating an outline of the process flow (step 5) of a network eyeglass ordering and marketing system for selecting ready-made presbyopic eyeglasses.

First, when the user interface unit 1 is connected to the eyeglass ordering and marketing service center 2, an ID code input window or a user authentication window is transmitted.

The user authentication window prompts the user to input user authentication information. The user interface unit 1 receives and displays the user authentication window, and allows user authentication information to be input and then sent to the eyeglass ordering and marketing service center 2.

The user authentication information includes a password, user ID and other suitable identifying information.

The eyeglass ordering and marketing service center 2 receives the user authentication information. Then, based on the information, the eyeglass ordering and marketing processor 23 or database controller retrieves data in the purchaser information database to perform authentication.

The eyeglass ordering and marketing service center 2 sends a basic attribute input window to the user interface unit 1 to allow the purchaser to input his or her basic attributes and personal information.

At the user interface unit 1, the purchaser inputs basic attributes such as his or her address, name, date of birth, and telephone number as well as description of his or her eye condition (e.g. having difficulty viewing near distances) and a request concerning eyeglasses in accordance with the basic attribute input window sent from the eyeglass ordering and marketing service center 2.

Based on the basic attributes of the purchaser sent by the user interface unit 1, the eyeglass ordering and marketing service center 2 retrieves his or her data in the user database which is controlled by the database controller to check whether the purchaser is registered as a user.

When it is determined from the result of the retrieval that the purchaser is a registered user, the process proceeds to step 2 shown in FIG. 4, in which vision test data controlled in the eyeglass ordering and marketing service center 2 is retrieved.

Based on the vision test data and frame and lens information data, which are controlled in the user database (the basket database), an inquiry window is sent to the user interface unit 1 to check whether new eyeglasses may be made according to the previous data of the purchaser.

When the same frame and lenses as the previous ones are acceptable, the user interface unit 1 allows the purchaser to click "the same frame as the previous one is acceptable" on the inquiry window, which is then sent from the user interface unit 1 to the eyeglass ordering and marketing service center 2.

On the other hand, if the purchaser wants new frames and/or new lenses, the process proceeds to a selection step, a vision test step and/or a lens selection step, which are described below.

In addition, if the purchaser has a doctor's prescription, the process proceeds to a prescription service step.

On the step selection window sent from the eyeglass ordering and marketing service center 2, the purchaser clicks "the frame selection step", "the vision test step", and "the lens selection step" to transmit the user's intention to the eyeglass ordering and marketing service center 2.

After the lens selection criteria has been identified in the vision test step or prescription service step, the process proceeds to the lens selection step.

In the eyeglass ordering and marketing service center 2, the user is retrieved in the user database according to the basic attributes which are input by the user via the basic attribute input window. If it is determined that the purchaser is not a registered user, an inquiry window for checking if the purchaser has a doctor's prescription is sent from the eyeglass ordering and marketing service center 2 to the user interface unit 1.

On the prescription confirmation window sent to the user interface unit 1 for checking if the purchaser has a doctor's prescription, the purchaser clicks "YES" if the purchaser has a doctor's prescription or "NO" if the purchaser does not.

If the purchaser has a doctor's prescription, that is, if "YES" has been clicked, the process proceeds to step 3 shown in FIG. 5, in which an inquiry window is sent from the eyeglass ordering and marketing service center 2 to the user interface unit 1 to check if the purchaser is going to send a scanned version of the prescription or to input the text data of the prescription.

On the prescription data input window sent from the eyeglass ordering and marketing service center 2, the purchaser may input data regarding his or her prescription. Alternatively, the purchaser may click a box section for scanning and sending the prescription to send the scanned image data to the eyeglass ordering and marketing service center 2.

Then, the eyeglass ordering and marketing service center 2 sends the data sequentially to the user interface unit 1 to allow the process to proceed to the frame selection step and/or the lens selection step.

If the purchase has no prescription prepared by an ophthalmologist or the purchaser has clicked "NO", the eyeglass ordering and marketing service center 2 sends an inquiry window for checking if the purchaser is over 40–45 years of age.

If the purchaser is over 40–45 years of age and "YES" is clicked, the eyeglass ordering and marketing service center 2 further sends an inquiry window to the user interface unit 1 to check if the purchaser has difficulty in viewing near distances.

If the user is aware of difficulty in viewing near distances and clicks "YES", the eyeglass ordering and marketing service center 2 judges that the user has presbyopia and then sends to the user interface unit 1 an inquiry window for checking if the purchaser desires to order presbyopic eyeglasses.

If the purchaser desires to buy custom-made eyeglasses and clicks "YES", the process proceeds to step 4' shown in FIG. 7. Then, the eyeglass ordering and marketing service center 2 sends the data sequentially to the user interface unit 1 to allow the process to proceed to the frame and lens selection steps.

On the other hand, if the purchaser has no subjective symptom of having difficulty in viewing near distances and clicks "NO", the process proceeds to the step 4' shown in FIG. 7. In this step, the eyeglass ordering and marketing service center 2 sends the data sequentially to the user interface unit 1 to allow the process to proceed to the frame and lens selection steps. Judging this case from the viewpoint of age, the purchaser seems to have presbyopia and thus has to go through an increased number of steps to select either presbyopic or bifocal eyeglasses.

On the other hand, if the purchaser does not desire to order custom-made presbyopic eyeglasses but desires to order ready-made presbyopic eyeglasses and clicks "NO", information indicating that ready-made eyeglasses are to be ordered is sent to the eyeglass ordering and marketing service center 2.

The eyeglass ordering and marketing service center 2 determines the lens number that can be judged from the purchaser's age. Then, the process proceeds to a ready-made presbyopic eyeglass ordering system (step 5 in FIG. 8) for readily providing presbyopic eyeglasses.

If the purchaser is not over 40–45 years of age and clicks "NO", the process proceeds to step 4 shown in FIG. 6, in which the process proceeds from the frame selection step and/or the vision test step to the lens selection step in the eyeglass ordering and marketing service center 2.

Subsequently, the lens selection step will be described below.

Suppose that the user has determined that the latest vision data can be used and clicks "the selection of lenses according to the latest vision data". Moreover, suppose that the user has alternatively determined that his or her lenses may be prepared according to the doctor's prescription and clicks "the selection of lenses according to the doctor's prescription". Furthermore, suppose that the user has alternatively determined that ready-made presbyopic eyeglasses may be used according to his or her age and clicks "the ready-made presbyopic eyeglasses may be employed". In these cases, the lens selection unit 26 permits the user to select lenses according to the respective data.

On the other hand, suppose that the user desires to take a remote vision test via the Internet even when the latest vision data or the doctor's prescription is available. In this case, a vision determination unit 28 instructs the process to proceed to a remote vision test step that uses a remote vision test system.

Now, the remote vision test system and the method therefor will be described.

Figure 11:
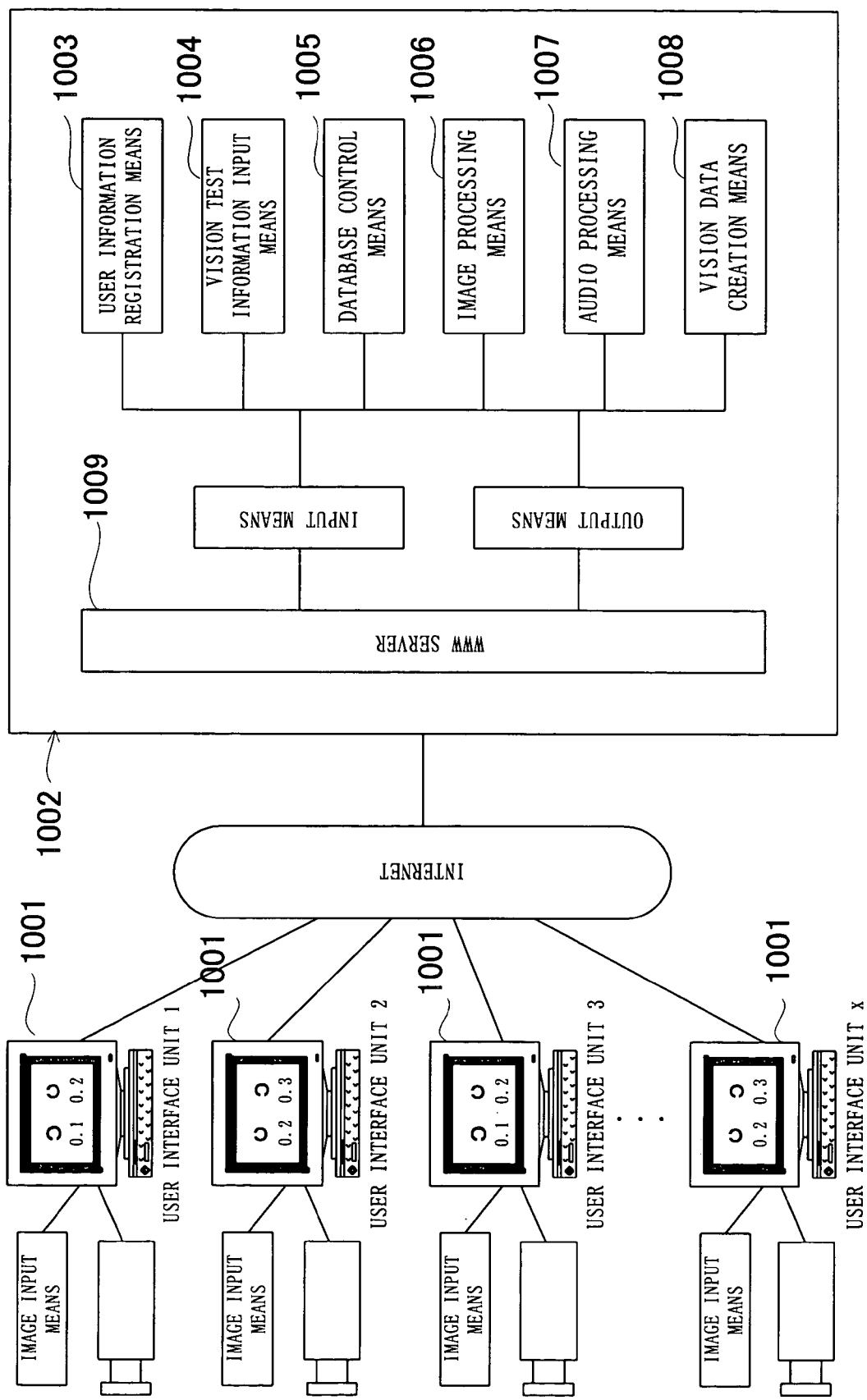
FIG. 11 is a view illustrating an exemplary configuration of a remote vision test system.
Figure 16:
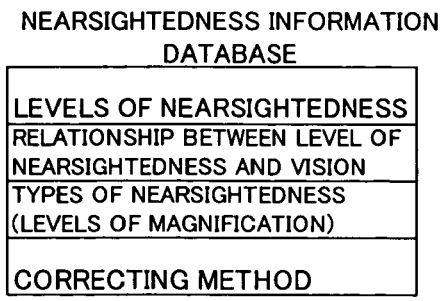
FIG. 16 is a view illustrating an exemplary configuration of a database including nearsightedness information which is controlled by a database controller at a service center.
Figure 17:
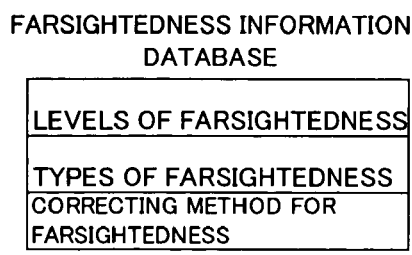
FIG. 17 is a view illustrating an exemplary configuration of a database including farsightedness information which is controlled by a database controller at a service center.
Figure 18:
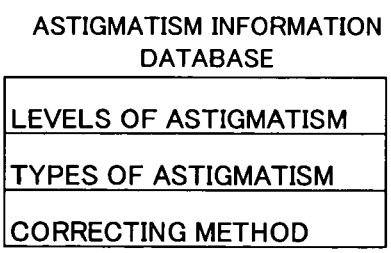
FIG. 18 is a view illustrating an exemplary configuration of a database including astigmatism information which is controlled by a database controller at a service center.

FIG. 11 is a view illustrating an exemplary configuration of the remote vision test system.

As shown in FIG. 11, the remote vision test system includes hardware such as a user interface unit 1001 and an electronic service center 1002, which are physically connected to each other via a network.

In the following description, the Internet is preferably used as the network to connect the user interface unit 1001 to the electronic service center 1002.

The remote vision test system extracts vision test data such as the level of nearsightedness, farsightedness, and astigmatism, based on reference data input from the user interface unit 1001 for testing vision. The remote vision test system also includes an output device for outputting vision test results containing the extracted data and includes the electronic service center 1002.

The electronic service center 1002 includes a vision test server, a user information registration units 1003, a vision test information input unit 1004, a database controller 1005, an image processor 1006, an audio processor 1007, a vision data creation unit 1008, and a WWW (World Wide Web) server 1009.

Specifically, the electronic service center 1002 includes information processing devices including personal computers, workstations, a server and other suitable devices.

In practice, the user information registration unit 1003, the vision test information input unit 1004, the database control unit 1005, the image processing unit 1006, the audio processing unit 1007, the vision data creation unit 1008, and the WWW server 1009 are each stored as a program in the memories of the information processing devices.

A database controlled by the database controller 1005 is stored in a storage unit such as a magnetic or an optical disk unit.

The electronic service center 1002 is connected to the user interface unit 1001 via a wide area computer network (the Internet).

The database controller 1005 controls information that is prepared by the electronic service center 1002 after being collected from the user interface unit 1001 by the user information registration unit 1003, the vision test information input unit 1004, the image processor 1006, and the audio processor 1007. The information is controlled and organized into a user information database, a reference database for testing vision, a vision test database, a vision table database, a nearsightedness information database, a farsightedness information database, and an astigmatism information database. The database controller 1005 also performs functions such as browsing information stored in a memory unit as the user information database, the reference database for testing vision, the vision test database, the vision table database, the nearsightedness information database, the farsightedness information database, and the astigmatism information database.

In addition, the database controller 1005 has an extraction unit for extracting data according to given conditions and a transmission unit for sending certain information to the user interface unit 1001.

The user information registration unit 1003 collects data regarding users or users desiring to take vision tests to register and control the data in the user information database. The data includes, for example, basic attributes such as addresses, names, dates of birth, telephone numbers, eye conditions (e.g., difficulty in viewing near distances), requests concerning eyeglasses, and data for identifying users such as user identifications (IDs), user passwords, and user codes.

In addition, user data required for identifying and sending messages to users such as facsimile numbers, e-mail addresses, and URLs are registered as well as data regarding computer environments.

The vision test information input unit 1004 determines and registers vision levels, based on data which is sent from user interface unit and includes reference for carrying out vision test.

The vision test information input unit 1004 also registers and controls each piece of data in the reference database for carrying out vision tests.

The image processor 1006 allows a scanner or other suitable device provided for (or connected to) the electronic service center 1002 to read the Landolt rings of a vision test table and allows the database controller 1005 to register and control the rings as a vision table database. In addition, the image processor 1006 transmits data to the user interface unit 1001 and displays the Landolt rings of the vision test table, which are registered and controlled in the vision table database.

The audio processor 1007 sends voice messages to users according to the window sent to the user interface unit 1001, and identifies the voice sent from the user interface unit 1001 to register and control the voice as data.

Based on the vision test references input at the user interface unit 1001, the vision data creation unit 1008 retrieves vision test data such as levels of nearsightedness, farsightedness, and astigmatism, and then creates vision test results including the retrieved data.

The WWW server 1009 includes a WWW server device for building homepages that are used as an interface to allow the user interface unit 1001 to have access to the database controller 1005 and other elements of the electronic service center 1002.

The WWW server 1009 includes a user authentication unit to verify a password and an identification (ID) if users who request to be registered to and browse databases controlled by the database controller 1005 are authorized users.

The user interface unit 1001 includes terminals used by users to apply for vision tests, the terminals being defined by personal computers or other suitable devices.

The user interface unit 1001 includes an I/O unit or an interface to a user or purchaser, and more specifically, may include input devices such as a keyboard and mouse, as well as output devices such as a CRT display.

The user interface unit 1001 includes access devices such as a WWW browser as an interface for exchanging various data with the WWW server 1009 of the electronic service center 1002. In the case where the user interface 1001 includes a personal computer, the WWW browser is defined by a program stored in the memory thereof.

Now, an example will be explained in which this system uses homepages on a network such as the Internet (a wide area computer network).

First, the electronic service center 1002 uploads a homepage on the Internet with the WWW server 1009.

With an access device such as a WWW browser of the user interface device 1001 that is connected to a wide area computer network, users access the user information registration unit 1003, which interfaces with the homepage of the electronic service center 1002, to send a request for vision tests.

The electronic service center 1002 allows the user authentication unit of the WWW server 1009 to verify that the user is an authorized registered member according to authentication information including the user's password and/or identification (ID). After the verification, the user information registration unit 1003 of the electronic service center 1002 writes in the user information database and controls the information that the user has sent for registration via the wide area computer network.

When it is determined that the user is accessing the vision test system for the first time, a basic attribute input window is sent to the user interface unit 1001. On the basic attribute input window, the user inputs basic attributes such as his or her address, name, date of birth, telephone number as well as eye conditions (difficulty in viewing near distances), requests concerning eyeglasses and other relevant information. Thus, the user interface unit 1001 allows the user to input necessary items, which are then sent to the electronic service center 1002.

In addition, the user also registers his or her password and/or member identification (ID) and other identifying information. Then, the user information registration unit 1003 writes the user information in the user information database via the wide area computer network and controls the information thus written therein.

FIGS. 12–18 illustrate an exemplary configuration of each database that is controlled by the database controller 1005 at the electronic service center 1002.

For example, as shown in FIG. 12, the user information database stores user information which is used to identify users and includes basic attributes such as user codes, user identifications (IDs), user passwords, addresses, names, dates of birth, and telephone numbers.

The user information includes the data that is input in the user information registration window sent to the user interface unit 1001 and that is registered by the user information registration unit 1003.

Incidentally, it is not always necessary to register data of all items.

User information identifications (IDs) and passwords may be determined at the service center according to the user information acquired off-line or may be automatically given at the time of an initial access by a user.

Data stored in the reference database for carrying out vision tests includes the purpose of use, age, previous lens magnification number, vision with lenses of the previous magnification number, balance between the right and left eyes with lenses of the previous magnification number, the period of service of the previous eyeglasses, the type of contact lenses (if used together with the eyeglasses), vision desired to be attained by correction, the presence of diseases associated with vision and other relevant information.

The vision test database stores data such as vision of uncorrected eyes, corrected vision, pupil distances, corrected levels of magnification for distance, corrected levels of magnification for reading, dates of test, and the name of a person who determines the level of magnification.

The vision table database stores data indicating the relationship between the levels of magnification and the Landolt rings.

In the nearsightedness information database, the levels of nearsightedness, the relationship between the level of nearsightedness and vision, types of nearsightedness (levels of magnification), and correcting method therefor are registered and controlled. Incidentally, the term "nearsightedness" is used for the eye that causes parallel beams of light incident to the eye with no adjustment made therefor to focus at a point in front of the retina (finite point in front of the retina).

The level of nearsightedness is expressed by the reciprocal of a far point distance (e.g., for a far point distance=50 cm, the level is equal to 1/0.5=2 D).

The relationship between the level of nearsightedness and vision is as follows:

TABLE 1

| Vision of uncorrected eyes | Level of nearsightedness | Corrected vision | Vision of uncorrected eyes | Level of nearsightedness | Corrected vision |
| --- | --- | --- | --- | --- | --- |
| 0.8 | −0.5 | 1.2 | 0.07 | −5.0 | 1.2 |
| 0.5 | −1.0 | 1.2 | 0.06 | −6.0 | 0.9 |
| 0.3 | −1.5 | 1.2 | 0.05 | −7.0 | 0.7 |
| 0.2 | −2.0 | 1.2 | 0.04 | −8.0 | 0.6 |
| 0.1 | −3.0 | 1.2 | 0.03 | −9.0 | 0.5 |

The types of nearsightedness (levels of magnification) are as follows:

minor nearsightedness (−4 D), moderate nearsightedness (−4 D to −7 D), severe nearsightedness (−7 D to −10 D), and very severe nearsightedness (−10 D or over).

The correcting method for nearsightedness is to wear an appropriate concave lens.

In the farsightedness information database, levels of farsightedness, types of farsightedness, and correcting method for farsightedness are registered and controlled. Incidentally, the term "farsightedness" is used for the eye that causes parallel beams of light incident to the eye with no adjustment made therefor to focus at a point behind the retina (finite point behind the retina).

The level of farsightedness is expressed by the reciprocal of a far point distance (e.g., for a far point distance=50 cm, the level is equal to 1/0.5=2 D).

The type of farsightedness is expressed by its level of magnification as follows:

minor farsightedness (+4 D), moderate farsightedness (+4 D to +7 D), and severe farsightedness (+7 D), the correction for which is to wear an appropriate convex lens.

In the astigmatism information database, levels of astigmatism, types of astigmatism, and correcting method for astigmatism are registered and controlled. Incidentally, the term "astigmatism" is used for the eye that causes parallel beams of light incident to the eye with no adjustment made therefor to focus at no point.

The types of astigmatism are as follows:

Regular astigmatism (Irregularity on the refraction surfaces is symmetrical.)

Irregular astigmatism (No image is formed due to different curvatures in the same meridian of the eye.)

Correcting methods for astigmatism are as follows:

Simple astigmatism (Wear an appropriate cylindrical lens.)

Compound astigmatism (Wear a cylindrical lens and a spherical lens in combination.)

Irregular astigmatism (Wear a contact lens.)

Now, a method for carrying out a vision test by the remote vision test system will be described below.

To begin with, the method for testing the vision of uncorrected eyes is described.

First, the user interface unit 1001 is connected to the service center 1002 to allow an ID code input window or a user authentication window to be transmitted. The user authentication window prompts the user to input user authentication information. The user interface unit 1001 receives and displays the user authentication window, and then the user inputs user authentication information, which is in turn sent to the electronic service center 1002.

The user authentication information includes a password, user ID and other identifying information.

The electronic service center 1002 receives the user authentication information and the database controller 1005 and the user information registration unit 1003 retrieve the user information from the user information database to verify the identity of the user.

In the service center 1002, the database controller 1005 transmits a service menu window or a user member top page to the user interface unit 1001.

The user interface unit 1001 in turn receives and displays the service menu.

Then, on the service menu window, the user clicks "vision test for uncorrected eyes" for testing the vision of uncorrected eyes.

Now, an outline of the method for testing the vision of uncorrected eyes is described.

(1) The user covers one eye with a hand to see the uncorrected eye vision test window (FIG. 19) with the other eye. On the uncorrected eye vision test window (FIG. 19), a point to be seen with one eye is displayed.

Figure 19:
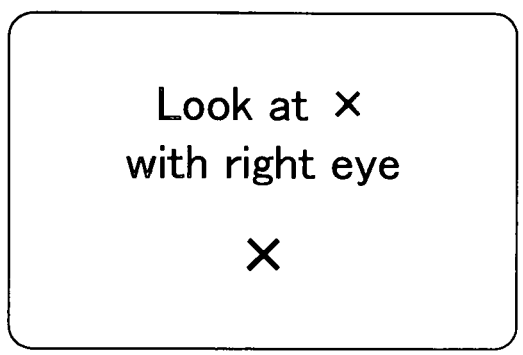
FIG. 19 is a view illustrating a screen for performing a vision test of uncorrected eyes of users.

(2) The user makes his or her neck stationary to maintain the same distance from the user to the uncorrected eye vision test window (FIG. 19). For example, in order to keep the face stationary, the user holds the neck on the hand palms with the elbows placed on a desk.

Then, in order to maintain the distance from the user to the uncorrected eye vision test window (FIG. 19), the user places one end of a 30-cm ruler on the window to set the distance to approximately 30 cm.

(3) The electronic service center 1002 allows the vision test information input unit 1004 to display a Landolt ring 1.0 of the vision test table at the point "X" on the window.

The electronic service center 1002 determines the distance from the user to the uncorrected eye vision test window (FIG. 19) using the vision test information input unit 1004, and displays a vision test table that corresponds to the vision 1.0.

(4) The user watches the Landolt ring of the vision test table (FIG. 20) with one eye.

(5) The electronic service center 1002 allows the vision test information input unit 1004 to display a question for the user on the window or the audio processor 1007 presents the question by voice, "Can you see the open side of the ring?"

(6) If the user can see it, the user clicks "YES" with a mouse (or responds by voice). In addition, the vision test information input unit 1004 of the electronic service center 1002 sends an interactive diagnosis window to the user interface unit 1001. A question "which side is open?" is displayed on the interactive diagnosis window to allow the user to click the mouse to choose (or answer by voice) the open side of the Landolt ring from the eight directions, that is, "up, down, left, right, upper left, lower left, upper right, and lower right directions". If the chosen direction is correct, a vision test table of a level of magnification 1.2 is displayed and then the same process is repeated.

(7) If the user cannot see the ring or has chosen a wrong direction of the opening, the electronic service center 1002 displays a vision test table having a lower level of magnification than the previous one to the user interface unit 1001 and then the same process is repeated.

(8) The electronic service center 1002 determines a correct level of magnification immediately before two consecutive errors as the uncorrected eye vision.

(9) Then, the same process is carried out on the other eye.

Now, the method for testing corrected vision is described.

(1) The electronic service center 1002 inputs uncorrected eye vision data on the homepage.

The uncorrected eye vision data includes:

Data that has been obtained through the vision test carried out on the network in the above-mentioned process of "the method for testing uncorrected eye vision";

Prescription data of an ophthalmologist; and

Previous vision test data controlled at the electronic service center 1002.

(2) The electronic service center 1002 transmits an after-correction vision test window to the user interface unit 1001 and displays the window there. The window displays the Landolt ring that the user may recognize with lenses that are expected, according to the above-mentioned uncorrected eye vision input, to provide each of the eyes with corrected vision of 1.2. In other words, "a Landolt ring that would be seen as such" is displayed on the after-correction vision test window.

(3) The user interface unit 1001 allows the user to see the Landolt ring displayed on the window of the user interface unit 1001 with one uncorrected eye while covering the other eye, and thus determines how the user sees the Landolt ring of a level of magnification around 1.2.

(4) When the user can see the ring well at the user interface unit 1001 and clicks "seen well", the electronic service center 1002 determines the level of magnification as the after-correction vision based on what has been transmitted from the user interface unit 1001.

When the user cannot see the ring well and clicks "not seen well", the electronic service center 1002 determines that the user has an astigmatism based on what has been transmitted from the user interface unit 1001, and then the process proceeds to the step of performing an astigmatism test.

In the step of performing an astigmatism test, the electronic service center 1002 sends to the user interface unit 1001 a vision test table indicating four Landolt rings each of which has an opening at the top, bottom, and 90 degrees to the left and right. Then, the user can determine his or her astigmatism and its axis, based on how the user sees the Landolt ring on the after-correction vision test window transmitted to the user interface unit 1001. The points for determining the level of magnification in testing astigmatism are as follows:

(1) Rotating a Landolt ring slowly makes it possible to check whether or not there is a position at which the opening of the Landolt ring disappears. If there is such a position, the user at the user interface unit 1001 clicks at this point with a mouse on the after-correction vision test window. With the position clicked, the electronic service center 1002 identifies the astigmatic axis (AXIS).

If the same test repeated several times yields a variation, the electronic service center 1002 sends to the user interface unit 1001 an after-correction vision test window, to which a spherical level of magnification (SPH) has been added, and repeats the same test.

If the opening of the Landolt ring does not disappear, the user at the user interface unit 1001 clicks on "the opening does not disappear" on the after-correction vision test window, so that the electronic service center 1002 determines that the user has no astigmatism.

(2) In addition, the electronic service center 1002 transmits a radial index image to the user interface unit 1001. Then, the user interface unit 1001 allows the user to determine the positions of the most and least dark lines on the after-correction vision test window and click the positions with a mouse, thereby allowing the electronic service center 1002 to identify the astigmatic axis (AXIS).

(3) After the astigmatism has been identified, a vision test table showing a Landolt ring after correcting for the astigmatism is displayed on the window to check how it is seen.

(1) The vision corrected to a level of magnification 1.2 is determined as the corrected vision. The corrected vision is so set that the user can choose from "exactly corrected=1.2", "roughly corrected=0.8", and "moderately corrected=1.0". Those who desire bifocal eyeglasses can take vision tests both for distance and for reading. For those who desire ready-made presbyopic eyeglasses, a level of magnification of presbyopia can be determined judging from their age. The system for determining levels of magnification in testing presbyopia is as follows.

(1) The user at the user interface unit 1001 inputs his or her age, occupation, use of eyeglasses, hobby, sport, present disease and so forth, on a questionnaire window transmitted from the electronic service center 1002 to the user interface unit 1001.

(2) Based on the user database of the electronic service center 1002, the level of magnification under the conditions described in (1) is determined in advance.

(3) By correlating (1) and (2), the applied level of magnification is determined.

Thus, for nearsightedness, data concerning the level of nearsightedness, the relationship between the level of nearsightedness and vision, and the type of nearsightedness (level of magnification) is extracted from the nearsightedness information database and displayed.

For farsightedness, data concerning the level of farsightedness and the type of farsightedness (level of magnification) is extracted from the farsightedness information database and displayed.

For astigmatism, data on the level of astigmatism, the relationship between the Landolt ring and level of magnification, and the relationship between Landolt ring and the astigmatism axis is extracted from the astigmatism information database.

Figures 20, 21:
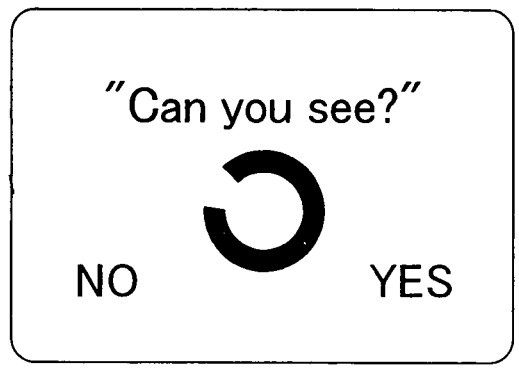
FIG. 20 is a view illustrating a screen for displaying a vision test table to users of the system.
FIG. 21 is a view illustrating the result of a vision test.

The results of vision test obtained at the electronic service center 1002 are transmitted to the user interface unit 1001 and displayed, for example, on a vision test result window as shown in FIG. 21.

DIST represents the level of magnification for distance and READ represents the level of magnification for reading.

SPH represents the spherical level of magnification, CYL represents the astigmatism level of magnification, AXIS represents the axis, and P.D. represents the distance from the center of the right eye to that of the left eye, that is, the pupil distance.

Incidentally, both levels of magnification for distance and reading are represented for the right eye (R) and the left eye (L).

According to this remote vision test system and the method therefor, anyone can have his or her uncorrected eye vision or after-correction vision tested via the Internet.

The electronic service center 1002 may be integrated with the eyeglass ordering and marketing service center 2 to share the unit having the same function for the remote vision test system to perform intensive processing. Alternatively, the electronic service center 1002 and the eyeglass ordering and marketing service center 2 may be adapted to perform distributed processing with a plurality of computers, servers, and other suitable elements.

The lens selection unit 26 of the eyeglass ordering and marketing service center 2 transmits a lens selection window for displaying lenses to the user interface unit 1. The lens selection window displays the lenses which are expected to comply with the user's request that the user has input at and sent from the user interface unit 1 and/or which the eyeglass ordering and marketing service center 2 recommends to the user. The lenses to be displayed on the lens selection window are chosen from various lenses registered in a database on the basis of the latest vision test data, doctor's prescriptions, and data obtained by the remote vision test system. If the user has already been registered, the lenses previously purchased are also displayed on the lens selection window.

The alternatives of the lenses include manufacturer's names, models, intended use, lens characteristics (thickness and weight of lens, durability, prevention of UV light), colors, prices, and levels of magnification and so forth. The user chooses a lens that the user wants to buy, and then inputs on the lens selection window the one that the user wants to buy, which is in turn transmitted to the eyeglass ordering and marketing service center 2.

The eyeglass ordering and marketing service center 2 performs the eyeglass ordering and marketing process using the lens selection unit 26, the eyeglass ordering and marketing processor 23, and the settling unit 24.

Now, the frame selection step will be described.

Suppose that data concerning the function and ornament of a frame exists at the eyeglass ordering and marketing service enter 2, such as when the user has already been registered. In this case, the frame can be registered in terms of fashion, image, design and so forth.

Now, it is explained below how to select the frame in the case where data relating to the function and aesthetics of the frame exists at the eyeglass ordering and marketing service center 2.

Frames are registered as a database at the eyeglass ordering and marketing service center 2. A frame selection window for displaying typical frames chosen from the database is transmitted by the frame selection unit 27 to the user interface unit 1.

Then, the user responds on the frame selection window to the inquiries in a questionnaire form including fashion, material, design, budget and so forth. Based on the data reflecting the user's requirements, the frame that is determined to be optimum is selected by the frame selection unit 27 in the eyeglass ordering and marketing service center 2. Then, the eyeglass ordering and marketing service center 2 sends the frame selection window to the user interface unit 1 again.

If the user has already been registered, the frame previously purchased is also displayed on the frame selection window.

The alternatives of the frame include fashion, material, design, price and other factors. The user selects a frame that the user wants to buy. Then, the user inputs the purchase of the frame that the user wants to buy on the frame selection window, which is in turn transmitted to the eyeglass ordering and marketing service center 2.

Now suppose that no data concerning the function of the frame exists in the eyeglass ordering and marketing service center 2 or the user wants to select a frame by having the frame, which the user wants to buy, put virtually on the face image of the user. In this case, the frame selection unit 27 instructs the user to proceed to a subsequent virtual eyeglass wearing experience step.

Now, the virtual eyeglass wearing system and the method therefor will be described.

Figure 22:
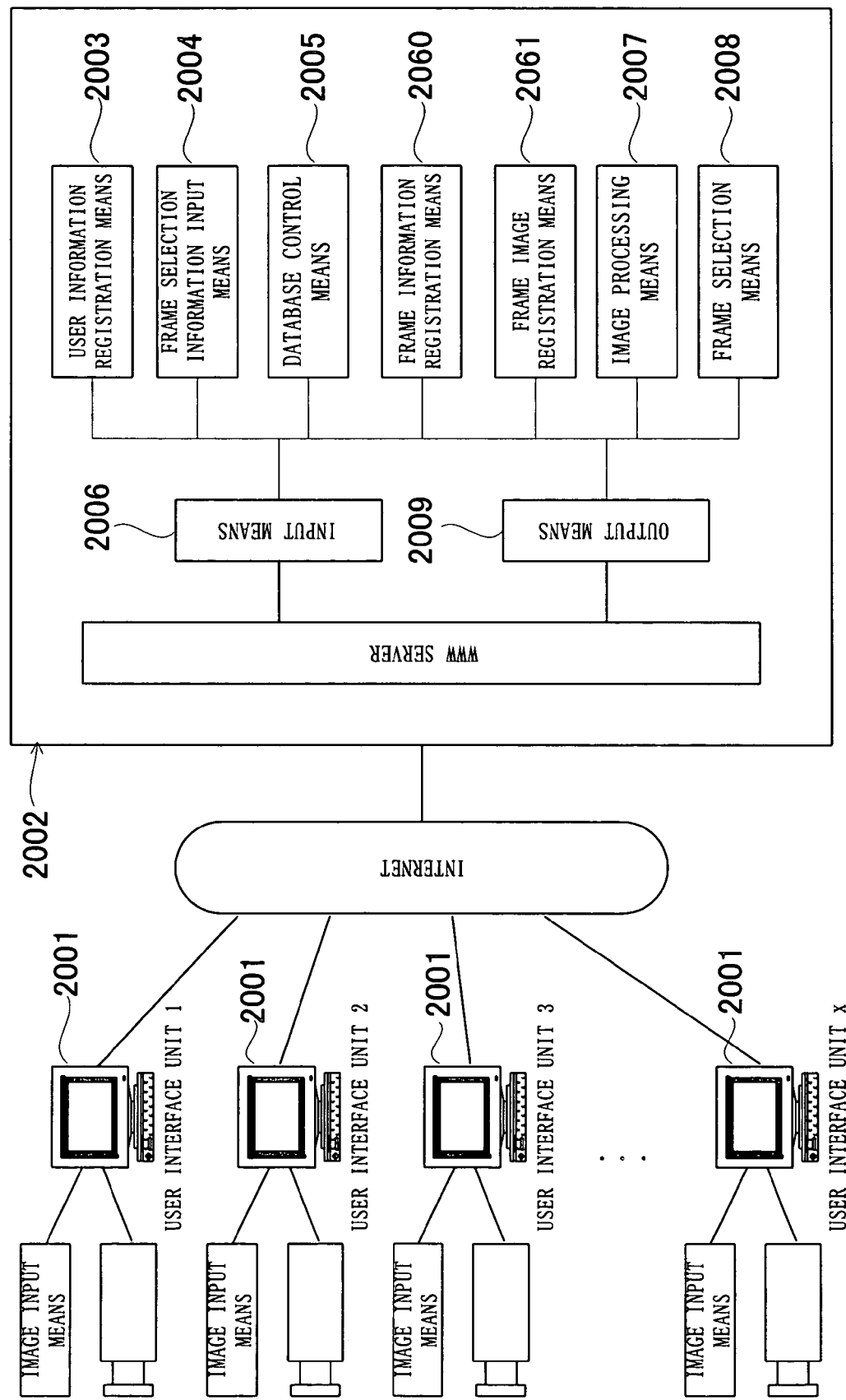
FIG. 22 is a view illustrating an exemplary configuration of a virtual eyeglass wearing system.

FIG. 22 shows a view illustrating an exemplary configuration of a virtual eyeglass wearing system.

The virtual eyeglass wearing system allows various types of eyeglass frames to be put on the image of user's face. The system includes a user interface unit 2001 and an electronic service center 2002.

These components are physically connected to each other via a network. In the following description, the Internet is preferably used as the network to connect the user interface unit 2001 to the electronic service center 2002.

The user interface unit 2001 is a terminal used by a user for putting various types of eyeglass frames on the image of the user's face using, for example, a personal computer. The user interface unit 2001 preferably includes an I/O unit or an interface to a user using the I/O unit. More specifically, the user interface unit 2001 preferably includes input devices such as a keyboard or a mouse and output devices such as a CRT display. The user interface unit 2001 also includes a WWW browser 2011 as an interface to the electronic service center 2002. When the user interface unit 2001 is a personal computer, the WWW browser 2011 is preferably defined by a program stored in the memory.

The electronic service center 2002 includes a user information registration unit 2003, a frame selection information input unit 2004, a database controller 2005, a frame information registration unit 2060, a frame image registration unit 2061, a frame selection unit 2008, an image processor 2007, an output unit 2009, and a server including a WWW server.

Specifically, information processing devices including personal computers, workstations, and a server or other suitable devices may be used. The electronic service center 2002 is preferably connected to the user interface unit 2001 via a wide area computer network (the Internet).

The WWW server builds homepages that are used as an interface by the user interface unit 2001 to access the database controller 2005 and other elements.

The WWW server also has a user authentication unit to check a password and an identification (ID) of a user to determine if a user who requests registration to and browsing through a database from the user interface 2001 is authorized. The database is preferably controlled by the database controller 2005.

At the electronic service center 2002, an input unit 2006 including devices such as a keyboard is used to input data about each frame provided by the electronic service center 2002. Then, text data about frame functional structures and frame ornamental structures is registered and controlled.

The frame image registration unit 2061 of the input unit 2006 at the electronic service center 2002 is used to input the image of frames that are provided by the electronic service center 2002. Then, the frame images input at the electronic service center 2002 are registered and controlled.

The user information registration unit 2003 of the electronic service center 2002 is used to register and control user information such as face images transmitted from the user interface unit 2001.

The database controller 2005 stores and controls user's face images input by the user information registration unit 2003, and frame images input by the frame image registration unit 2061 of the input unit 2006.

The frame selection unit 2008 of the electronic service center 2002 is adapted to select a suitable frame functional structure, a frame ornament, and a frame image for each frame in the database controller 2005, which are stored by the frame information registration unit 2060. In this case, the selection is performed based on the frame selection references that are controlled by the database controller 2005, that is, functional structure data, ornamental structure data, and face image data for selecting a frame that the user desires. The frame selection unit 2008 is further adapted to create or select frame images for displaying eyeglass frames of different types.

The image processor 2007 of the electronic service center 2002 is adapted to output an eyeglass wearing image in which an eyeglass frame image selected by the above-mentioned frame selection unit 2008 is combined with a face image data controlled by the database controller 2005.

The user interface unit 2001 includes a terminal used by a user and is, for example, a personal computer.

The user interface unit 2001 in this preferred embodiment preferably includes a personal computer as the main component and is further provided with a CRT or a head mounted display (HMD) as an image display unit capable of displaying view images. It is possible to use other methods and devices for displaying images such as screen projection or laser irradiation. Moreover, a keyboard is preferably used as an information input device. However, it is possible to use various types of input devices such as pointing devices such as mice, track balls, or joysticks, touch panels, switches or other suitable devices.

Furthermore, a digital camera is preferably provided as an image input device. However, any device such as television cameras, video cameras, or digital still cameras may be used as long as they allow image information to be digitized for input. In addition, a hard disc and a CD-ROM drive are provided as a storage unit for storing images or other information, making it possible to use image information, programs or other information which are stored in CDs. It is also possible to use devices for storage media such as DVDs, MOs, or memory units. Furthermore, the personal computer according to this preferred embodiment is preferably connected to the Internet or a computer network (network), such that image information, software, or other information is transmitted and received via the network.

A computer that is a main component of the electronic service center 2002 first receives a command for operating the virtual eyeglass wearing system from a keyboard. The computer also includes the user information registration unit 2003 capable of receiving data such as personal information about users and display parameters of view images or a command for selection and the frame selection information input unit 2004. The computer further includes the frame image registration unit 2061 for receiving the input of image data digitized from a digital camera of the user interface unit 2001. The computer further includes the image processor 2007 for performing image processing according to the input data to select or create an appropriate virtual eyeglass wearing image. Moreover, the computer is provided with the database controller 2005 that stores and controls software of the virtual eyeglass wearing system, image information, view image samples that can be selectively displayed. View images that have been created or selected by the image processor 2007 are output from the output unit 2009 to be displayed on a CRT or HMD of the user interface unit 2001.

Now, a situation in which this system is implemented through a homepage on a network such as the Internet (a wide area computer network) is described.

First, the electronic service center 2002 uploads a homepage on the Internet with the WWW server. With an access device such as a WWW browser of the user interface unit 2001 connected to a wide area computer network, a user accesses the frame selection information input unit 2004 having an interface defined by a homepage of the electronic service center 2002. Then, the user sends a request for registration of frame selection reference data.

The electronic service center 2002 allows the user authentication unit of the WWW server to verify that the user has been authorized and registered, based on the user authentication information such as the user's password and/or identification (ID) and other identifying information.

Subsequently, the frame selection information input unit 2004 of the electronic service center 2002 writes in a storage unit and controls the selection reference information that has been requested from the user for registration via the wide area computer network.

The electronic service center 2002 also transmits an input window of basic attributes of the user to the user interface unit 2001. On the user basic attribute input window transmitted to the user interface unit 2001, the user inputs basic attributes of the user such as the user's name, address, date of birth, telephone number, eye conditions (e.g., difficulty in viewing near distances), and requests concerning eyeglasses.

The user further inputs selection criteria for a frame such as fashion, budget, function and condition of fit to the user's face into the user basic attribute input window sent from the electronic service center 2002.

The electronic service center 2002 stores and registers the user's basic attributes, selection criteria for a frame and other suitable information, as shown in each database structure illustrated in FIGS. 23–26, controlled by the database controller 2005.

Face images input by an image input device of the user interface unit 2001 are also transmitted to the electronic service center 2002.

Incidentally, when a face image is input with the image input device, a ruler or other measuring device is placed under the face to allow the face image to be input in conjunction with the ruler.

Based on the front view and side views (both sides) of the face image sent to the electronic service center 2002, the electronic service center 2002 creates frame selection criteria.

That is, based on the text data and the image data transmitted from the user interface unit 2001, the frame selection information input unit 2004 of the electronic service center 2002 creates the functional structure data and ornamental structure data of a frame. Then, the database controller 2005 stores and controls the data in the storage unit.

The frame functional structure data includes, for example, the distance between the right and left pupils, the widths from the center of the right and left pupils to the base of the ears, and the opening angles of temples determined based on the widths from the center of the right and left pupils to the base of the ears. Also included are the distances from the base of the ears to the tops of the corneas, the bending positions of the temples, the distances between the tops of the corneas and the base of the nose, the opening angles of pad bridges determined based on the distances between the tops of the corneas and the base of the nose, budgets and so forth.

Moreover, based mainly on text data such as selection criteria (sense of fashion and condition of fit to the face) transmitted from the user interface unit 2001, the frame selection information input unit of the electronic service center 2002 also creates frame ornamental structure data. Then, the frame ornamental structure data is stored in the storage unit and controlled by the database controller.

The frame ornamental structure data includes shapes such as Wellington, Lloyd, Oval, Square, Tonneau, Boston, Butterfly, and Auto (Drop). Materials are rimless (two-point, three-point), metal+nylon rimmed, celluloid+nylon rimmed, metal, celluloid, brow-line, combination and so forth. Brands include various brands, and colors include various colors.

At the electronic service center 2002, text data concerning the frame functional structure data and the frame ornamental structure data for each of the frames that can be supplied is registered and controlled by the input unit 2006 such as a keyboard and the frame image registration unit 2061. The frame images input from the frame image registration unit 2061 of the input unit 2006 at the electronic service center 2002 are registered and controlled.

The frame functional structure data of each frame includes a size or an actual size (44F–62F), and features such as a shape-memory alloy, super-light weight, super-elasticity, simultaneous function as sunglasses, portability and so forth. Also included are functions such as the distance between the right and left pupils, the widths from the center of the right and left pupils to the base of the ears, the opening angles of temples determined based on the widths from the center of the right and left pupils to the base of the ears, the distances from the base of the ears to the tops of the corneas, the bending positions of the temples, the distances between the tops of the corneas and the base of the nose, and the opening angles of pad bridges determined based on the distances between the tops of the corneas and the base of the nose.

The frame ornamental structure data includes shapes such as Wellington, Lloyd, Oval, Square, Tonneau, Boston, Butterfly, and Auto (Drop). Materials are rimless (two-point, three-point), metal+nylon rimmed, celluloid+nylon rimmed, metal, celluloid, brow-line, combination and so forth. Brands include various brands, and colors include various colors.

The user information registration unit 2003 of the electronic service center 2002 registers and controls face images transmitted from the user interface unit 2001. Frame images input from the frame image registration unit 2061 of the input unit 2006 at the electronic service center 2002 are registered and controlled.

The database controller 2005 stores user face images input by the user information registration unit 2003 and frame images input by the frame image registration unit 2061 of the input unit 2006.

The frame selection unit 2008 of the electronic service center 2002 selects a suitable frame functional structure, a frame ornament, and a frame image for each frame in the database controller 2005, which are stored by the frame information registration unit 2060. In this case, the selection is performed based on the frame selection references that are controlled by the database controller 2005, that is, functional structure data, ornamental structure data, and face image data for selecting a frame that the user wants. The frame selection unit 2008 further creates or selects frame images for displaying some eyeglass frames of different types.

The image processor 2007 of the electronic service center 2002 is adapted to output an eyeglass wearing image in which an eyeglass frame image selected by the above-mentioned frame selection unit 2008 is combined with a face image data controlled by the database controller 2005.

Then, the eyeglass-wearing image combined by the image processor 2007 is adapted to be output to each user interface unit 2001 by the WWW server via the Internet.

Now, the method for the user to wear various eyeglasses using the above-mentioned virtual eyeglass wearing system is described below.

First, when the user interface unit 2001 is connected to the electronic service center 2002, an ID code input window or a user authentication window is transmitted.

The user authentication window prompts the user to input user authentication information.

At the user interface unit 2001, the user authentication window is displayed, and then the user inputs user authentication information to be transmitted to the electronic service center 2002.

The user authentication information includes a password, user ID and other suitable identifying information.

The electronic service center 2002 receives the user authentication information, based on which the database controller 2005 and the user information registration unit 2003 retrieve in the user information database to perform authentication.

When it is determined that the user is using the system for the first time, a window for inputting basic attributes is further transmitted from the electronic service center 2002 to the user interface unit 2001.

Based on the window transmitted from the electronic service center 2002, the user at the user interface unit 2001 inputs basic attributes of the user, such as the user name, address, date of birth, and telephone number.

The electronic service center 2002 receives the basic attributes of the user, based on which the database controller 2005 and the user information registration unit 2003 creates a user information database and registers the password, the user ID and so forth.

Then, the service center 2002 transmits a frame selection reference window for inputting frame selection criteria to the user interface unit 2001.

The frame selection reference input window is used by a user to input criteria (such as the sense of fashion, budget, function, condition of fit to the face) for selecting a frame.

The user inputs frame selection criteria such as the sense of fashion, budget, function, condition of fit to the face and other criteria on the frame selection reference input window at the user interface unit 2001.

Subsequently, after the user has completed inputting the frame selection criteria in text data, a window prompting the user to transmit the user face image is further transmitted from the electronic service center 2002 to the user interface unit 2001.

The user takes the front view and side views (right and left sides) of the user face image into the user interface unit 2001 with an image input device such as a digital camera or a scanner.

Then, the front and side views of the user face image are transmitted from the user interface unit 2001 to the electronic service center 2002 via the Internet.

The electronic service center 2002 allows the frame selection information input unit 2004 to receive the text data and image data (the face image of the user), which are frame selection criteria sent from the user interface unit 2001, and the database controller 2005 to register and control the data.

Figure 27:
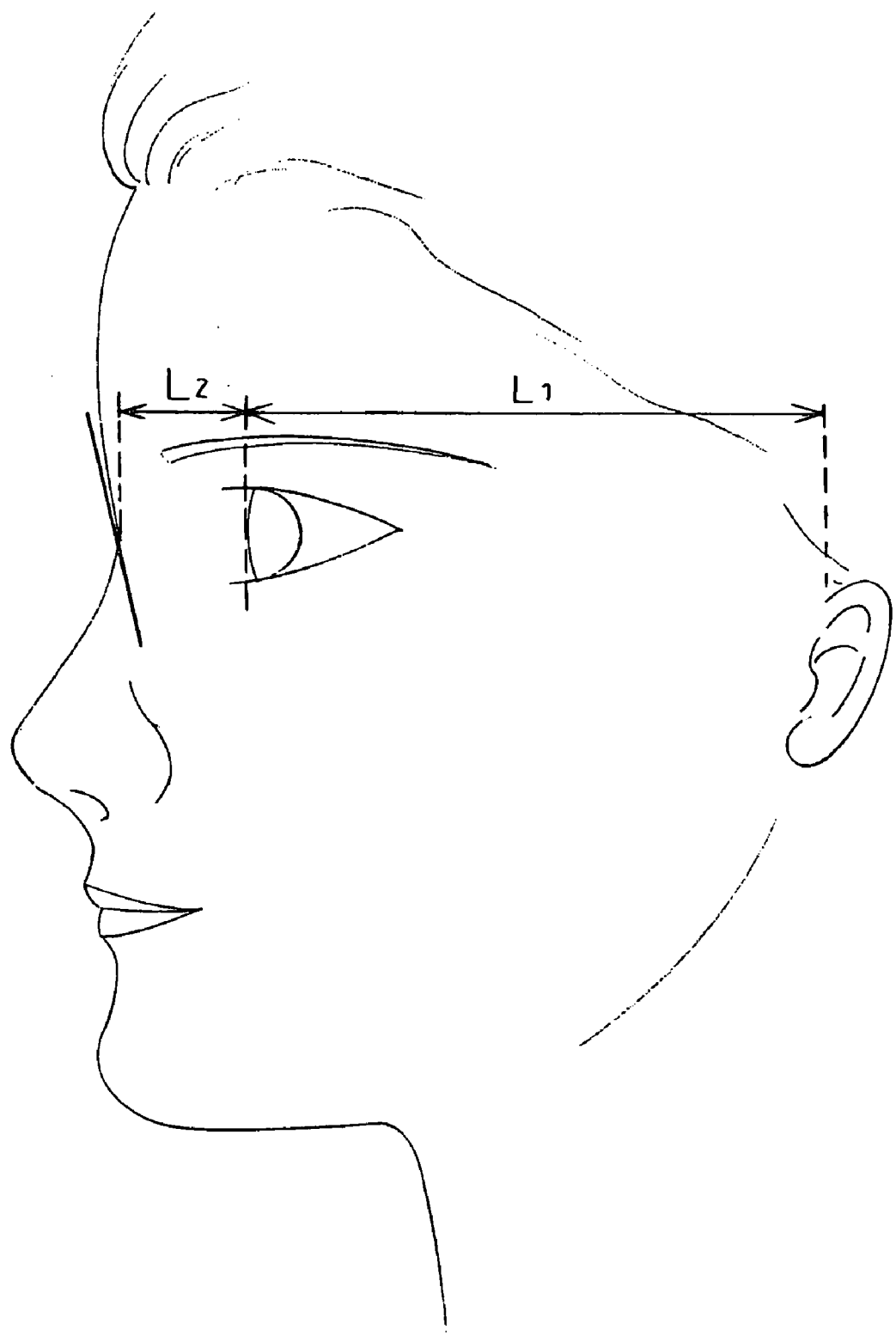
FIG. 27 is a diagrammatic view illustrating a measuring method on a side of a face image.

(1) Based on the side images (FIG. 27) of the user, the distances ($L_1$) between the base of the ears and the tops of the corneas of the user are measured separately for the left and right, and the resulting data is registered and controlled by the database controller 2005. Based on the aforementioned measurements, the positions at which the temples are bent are determined separately for the left and right, and then registered.

(2) Based on the side images of the user, the distances ($L_2$) between the tops of the corneas of the user eyes and the base of the nose are measured, and an average value of the left and right distances is registered and controlled in the database controller 2005. The distance $L_2$ is usually 12 mm. The frame selection information input unit 2004 determines and registers the opening angles of the pad bridges, based on the above measurements.

(3) Based on the front image (FIG. 28) of the user, the widths ($L_3$) from the center of the pupils of the right and left eyes to the base of the ears are measured separately for the left and right, and are then registered and controlled by the database controller 2005. Based on the above measurements, the frame selection information input unit 2004 determines and registers the opening angles θ of the temples separately for the left and right.

For the widths from the center of the pupils of the right and left eyes to the ears, the distance between the pupils (PD) is first determined. However, at the electronic service center 2002, the pupils cannot be precisely detected on the user face image, and therefore the distance between the pupils (PD) is approximated, for example, from the distance ($PD_1$) between the left side of the left eye and the left side of the right eye.

The pupils cannot be detected from the face image. Therefore, to determine the distance ($L_4$) between the pupil of the left eye and the left ear, the distance from the base of the left ear to the right side of the left eye (La) and the distance from the base of the left ear to the left side (Lb) of the left eye are determined. Then, the distance ($L_4$) between the pupil of the left eye and the left ear is determined by calculation. The distance between the right eye and the right ear can also be determined in the same manner.

Figure 28:
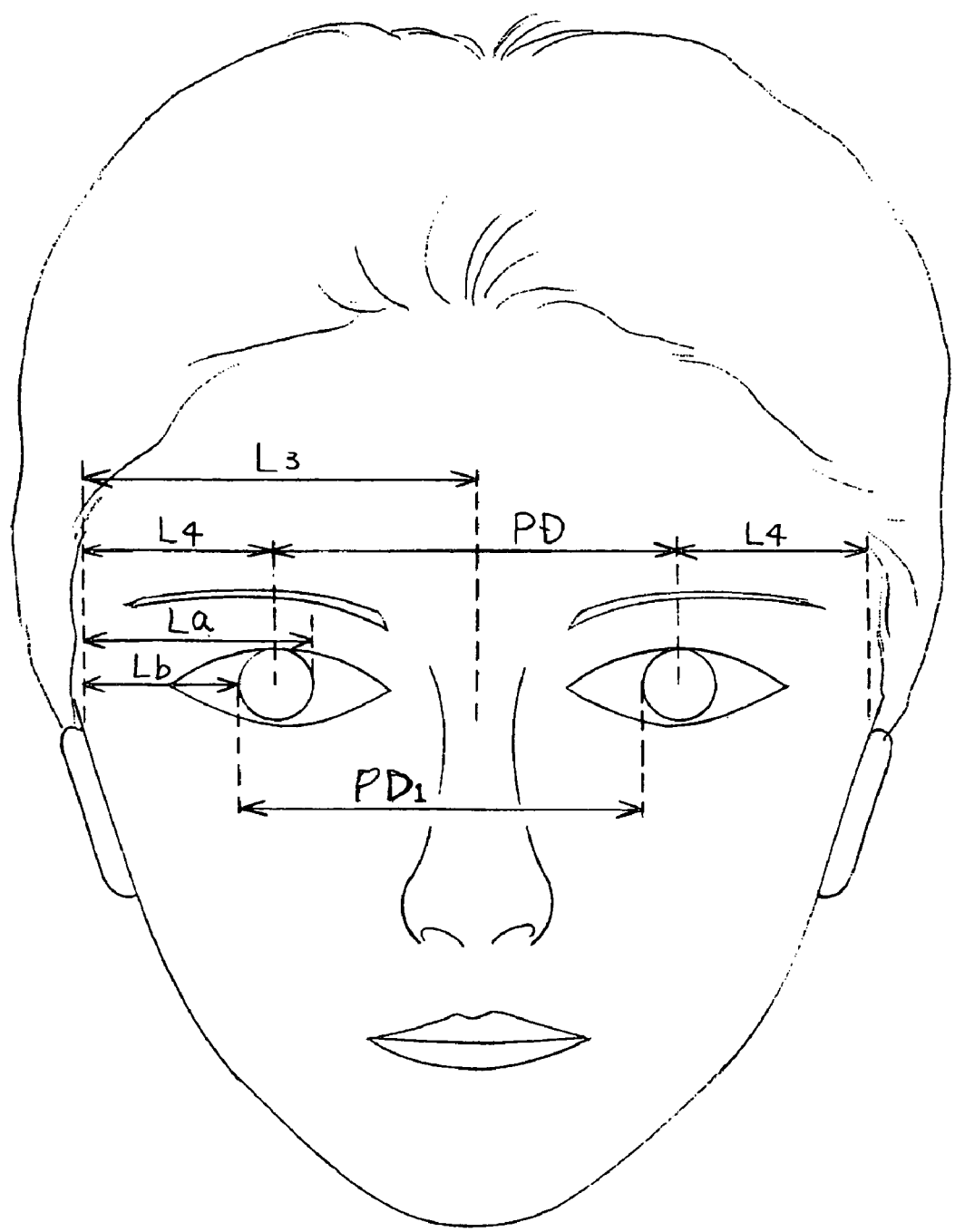
FIG. 28 is a diagrammatic view illustrating a measuring method on the front of a face image.
Figure 29:
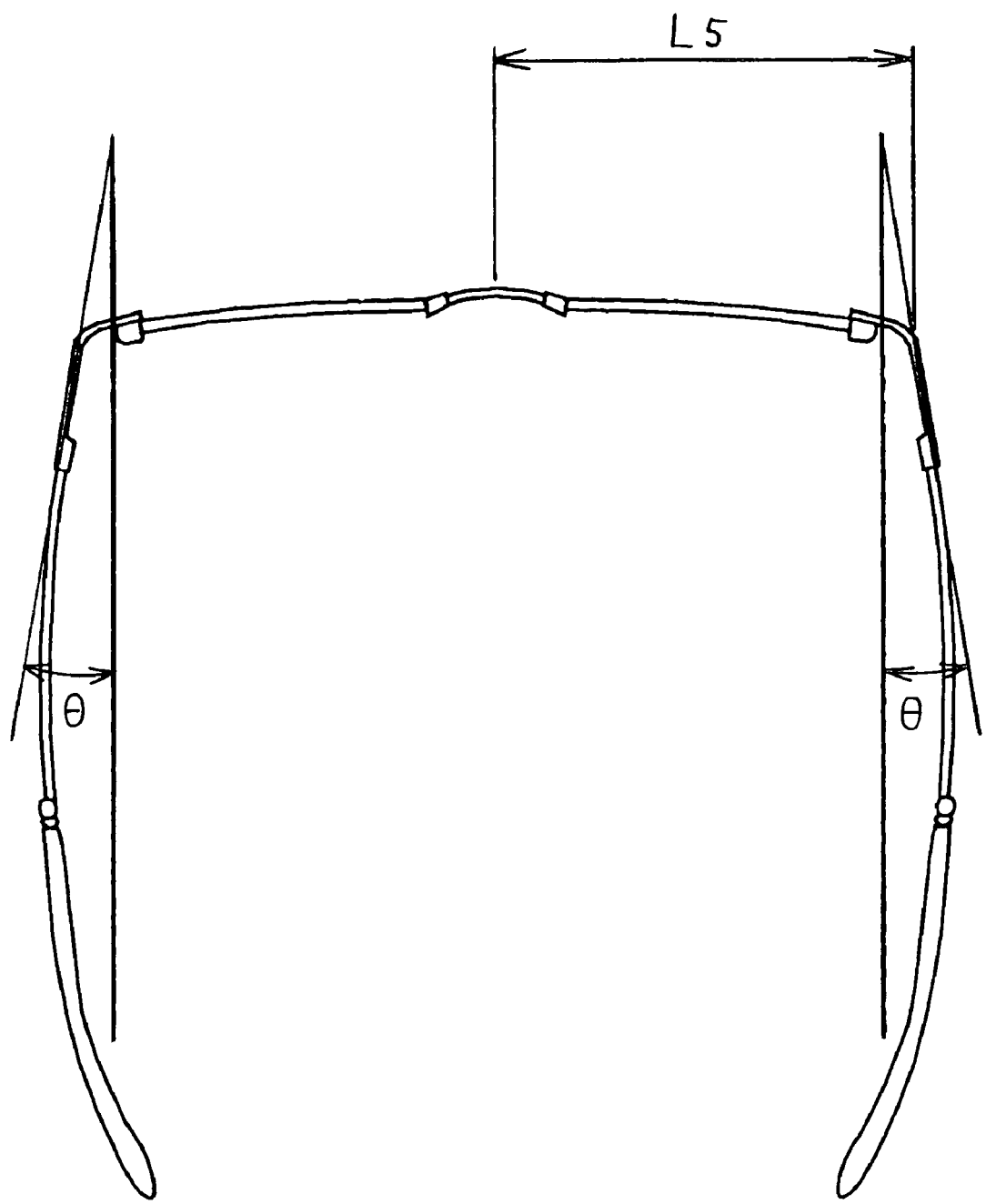
FIG. 29 is a diagrammatic view illustrating a method for adjusting frames.

The opening angles θ of the left and right temples of the eyeglass frame are adjusted, for example, by correcting and bending the temples by the amount of angle obtained from the following equation.

$$PD/2 + L_4 - L_5$$

where $L_5$ is the front size of the eyeglass frame (Refer to FIGS. 28 and 29).

(4) When bifocal lenses are specified, an additional bending angle of 5 degrees is provided for the angle of inclination of the lens surface. For this reason, the opening angle of the pad bridges is determined and registered by being corrected with the additional angle of bending.

Thus, at the service center 2002, the central processing unit and the frame selection information input unit 2004 perform computation to create functional structure data, ornamental structure data, and face image data, which are in turn stored by the database controller 2005 in conjunction with the face image data.

At the electronic service center 2002, the frame information registration unit 2060 and the frame image registration unit 2061 input and store in advance the frame functional structure, the frame ornamental structure, and the frame image of each frame in the database controller 2005. Based on the frame functional structure, the frame ornamental structure, and the frame image of each frame registered by the database controller 2005 through the frame information registration unit 2060 and the frame image registration unit 2061, an appropriate frame is selected corresponding to the functional structure data, ornamental structure data, and face image data according to the frame selection criteria transmitted from the user interface unit 2001.

The frame selection unit 2008 creates or selects frame images for displaying eyeglass frames of different types. Thereafter, the image processor 2007 of the electronic service center 2002 creates an eyeglass-wearing image in which the image of the frame that fits the face image of the user is combined with the face image of the user.

Then, the eyeglass-wearing image in which the face image of the user is combined with the frame image, which is created by the image processor 2007, is transmitted from the output unit 2009 (the WWW server) to the user interface unit 2001 via the Internet.

The user can check the image transmitted to the user interface unit 2001 to see if the frames are similar to those that the user has requested and how the user's face looks with the frames thereon at the eyeglass-wearing window.

Suppose that the frames are different from those that the user has requested or the user wants to see the face with different frames thereon. In this case, the user further inputs a message to the eyeglass wearing window sent from the electronic service center 2002 and transmits the message to the service center 2002.

The electronic service center 2002 selects different frames in the same manner as the one mentioned above, and again transmits an eyeglass-wearing window from the WWW server to the user interface unit 2001 via the Internet.

According to the virtual eyeglass wearing system and the method therefor, the user can put various eyeglass frames on photographic data. Moreover, the user can try on various eyeglass frames at home via a network such as the Internet without going out to an eyeglass shop and select optimum frames that meet the user's own preference.

The user cannot usually see his or her face with eyeglass frames thereon from a third person's point of view. However, according to this system and method, the user can select frames with the selected eyeglass frames on his or her face while the user wears his or her own eyeglasses or contact lenses, that is, with an adequate vision. Thus, the user can select eyeglass frames that best fit the user.

Incidentally, the electronic service center 1002 and 2002 may be integrated into the eyeglass ordering and marketing service center 2, a single computer, and a server to perform processing. Alternatively, they may perform distributed processing with a plurality of computers and servers.

Figure 30:
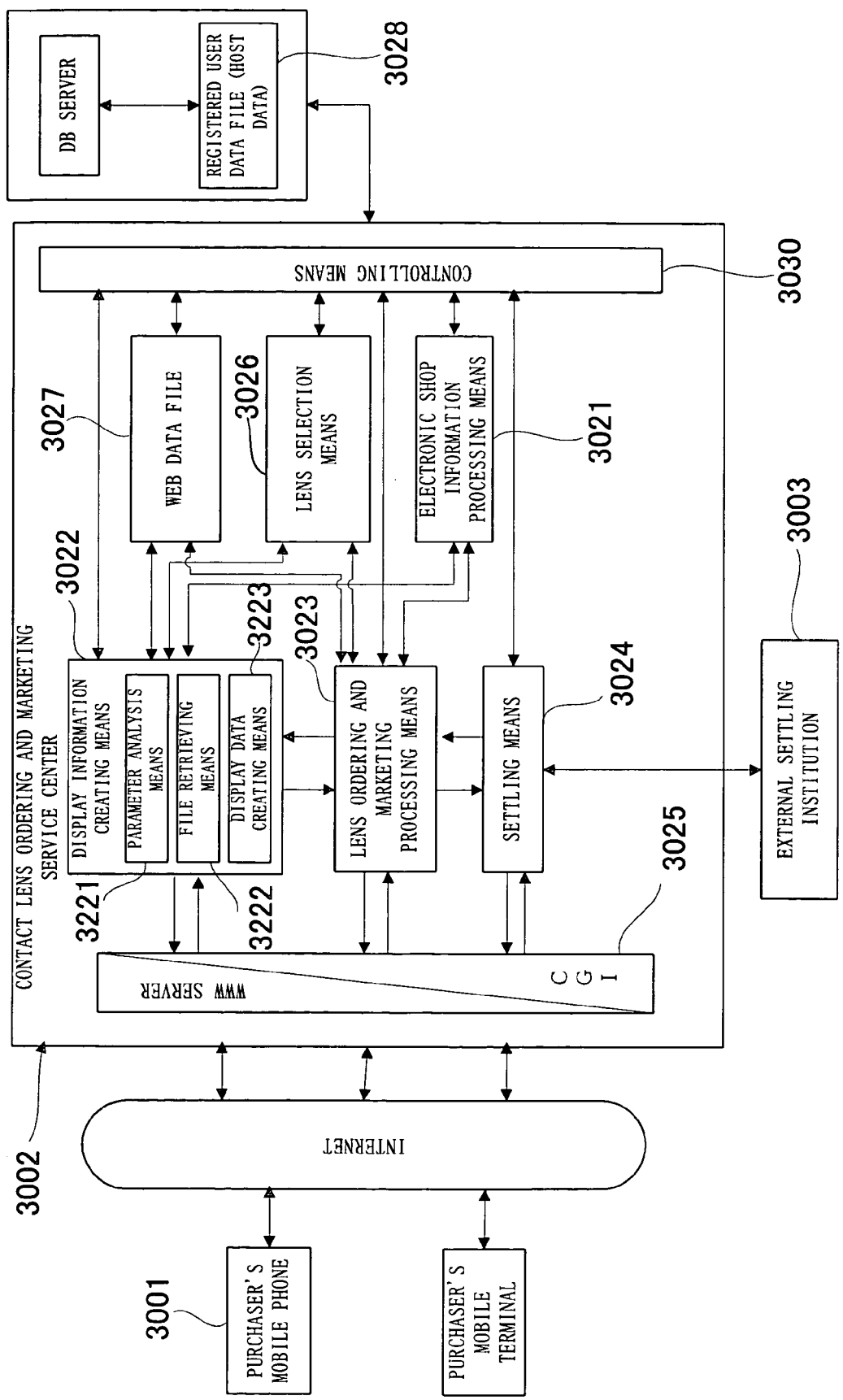
FIG. 30 is a view illustrating an exemplary configuration of a network contact lens ordering and marketing system.
Figure 31:
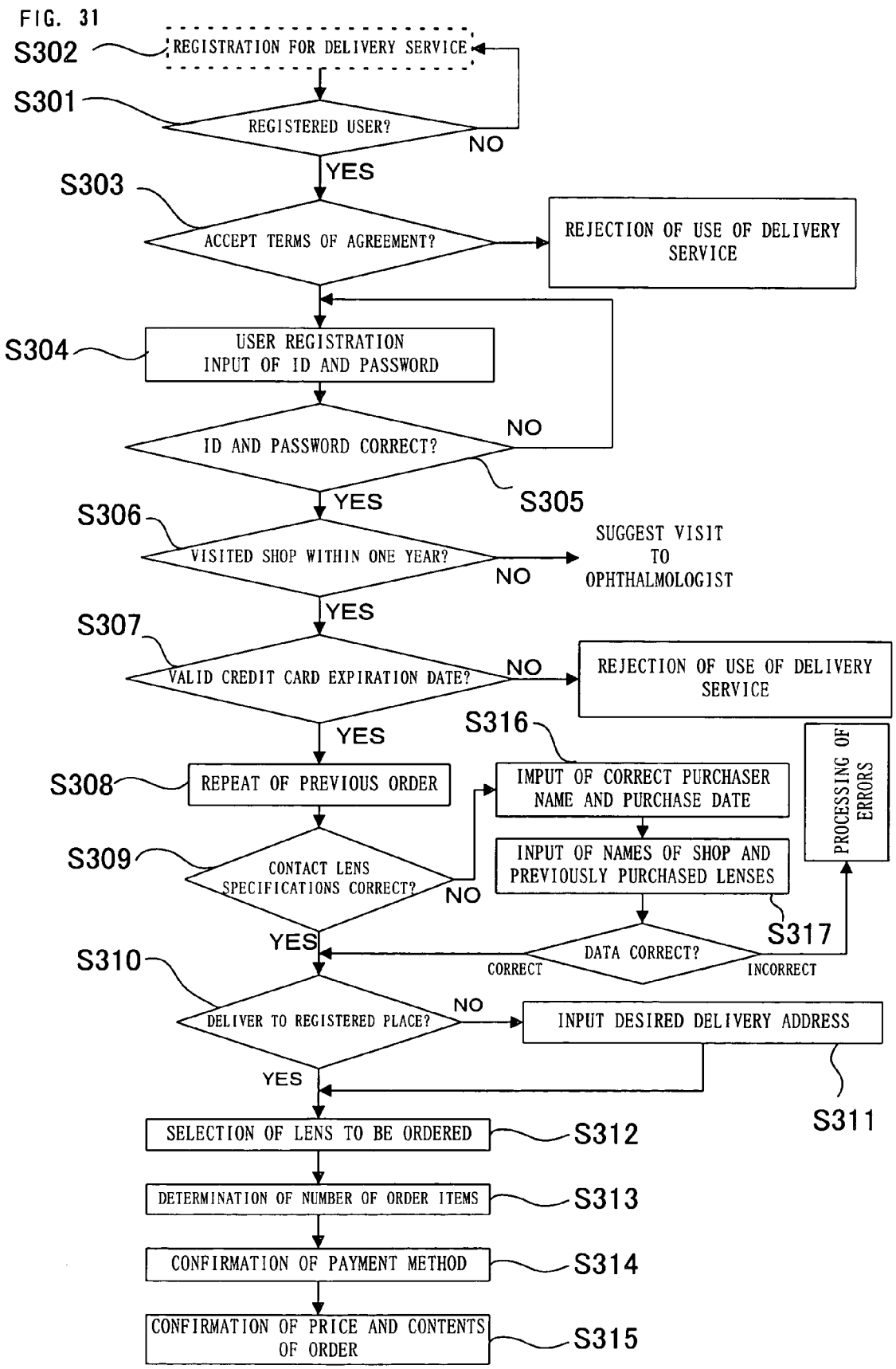
FIG. 31 is a view illustrating an outline of a flow of processing of a network contact lens ordering and marketing system.

FIG. 30 is a view illustrating an exemplary configuration of a network contact lens ordering and marketing system according to a preferred embodiment of the present invention.

As shown in FIG. 30, the system includes a mobile interface 3001 and hardware defining a contact lens ordering and marketing service center 3002.

These components are operatively connected to each another via a network.

The network connecting the mobile interface 3001 and the contact lens ordering and marketing service center 3002 includes the Internet, mobile communication networks, telephone lines, and other equipment.

The network contact lens ordering and marketing system is capable of marketing contact lenses with strength adjusted to the vision or requests of those who place contact lens orders, and includes the contact lens ordering and marketing service center 3002.

The mobile interface 3001 is a mobile phone or other mobile information terminal for use of known services such as i-mode®, J-phone sky walker®, C-mail®, sky message®, and is used by a purchaser for placing an order for and obtaining their contact lenses via a network.

The mobile interface 3001 is an interface between a user or prospective purchaser and the service center, and includes an I/O device. More specifically, the I/O device is defined by an input device such as a keyboard and an output device such as a liquid crystal display.

Furthermore, the mobile interface 3001 is adapted to be connected to a computer network (network) or the Internet, such that image information, software, or any other information or data can be transmitted and received via the network.

Moreover, the mobile interface 3001 includes a WWW browser as an interface to the server of the contact lens ordering and marketing service center 3002.

The contact lens ordering and marketing service center 3002 includes an electronic shop information processor 3021, a display information creating unit 3022, a contact lens ordering and marketing processor 3023, a settling unit 3024, and a WWW server/CGI 3025.

Specifically, the contact lens ordering and marketing service center 3002 includes information processing devices such as personal computers, workstations, and servers. The electronic shop information processor 3021 is stored in a storage unit such as a magnetic or optical disk unit of the information processing devices. In practice, each of the processors mentioned above, i.e., the WWW server/CGI 3025, the display information creating unit 3022, the contact lens ordering and marketing processor 3023, and the settling unit 3024 is stored for execution in a program format in the memory of the information processing device.

The electronic shop information processor 3021 defines product data such as contact lenses and related goods, which are provided in the contact lens ordering and marketing service center 3002, in a product definition division via an I/O unit. The product data defined here are stored in a product database as product data information.

In this preferred embodiment, the product data information includes the shelves on which products such as contact lenses are exhibited, product numbers, product names, prices, product descriptions of e.g. contact lenses, text data such as product control information, and image data of products such as contact lenses and related goods. The contact lens ordering and marketing service center 3002 also preferably includes an I/O unit which serves as an interface to creators of electronic catalogs. The I/O unit accepts the input of product information including text data such as product shelves, product items, and prices, which are required for product definition, or image data showing product shapes, from the creators of the catalogs. As order information on products purchased by purchasers, the contact lens ordering and marketing service center 3002 also outputs information which includes information about products such as product numbers or quantities, information on addressees of products, and information on payment such as names of external settling institutions, payment dates, or the amount of payment. The contact lens ordering and marketing service center 3002 can be set up by an information processing device such as a personal computer including I/O devices such as a keyboard, a mouse, a CRT display or other suitable devices. In this case, the product definition division is defined by a program stored for execution in the memory of such an information processing device.

The electronic shop information processor 3021 is provided with an electronic open shop information unit that includes a shop database, a product database, and a basket database.

The shop database stores information for opening electronic shops and information for defining shop layouts to display product information.

The product database stores product data information that has been defined.

On the other hand, the basket database accumulates the information of a product, the purchase of which has been instructed from the mobile interface 3001.

The electronic shop information processor 3021 performs the function of storing transferred product data information into the product database.

The display information creating unit 3022 creates display information such as electronic catalogs in response to a request from the mobile interface 3001.

The display information creating unit 3022 includes a parameter analysis unit 3221, a file retrieving unit 3222, and a display data creating unit 3223.

The parameter analysis unit 3221 analyzes data such as vision test data, which are received from the mobile interface 3001 via the WWW server/CGI 3025, and extracts parameters included therein.

Based on the parameters extracted by the parameter analysis unit 3221, the file retrieving unit 3222 retrieves data that has been registered and stored in each database by the electronic shop information processing unit 3021.

The display data creating unit 3223 creates display data that can be displayed as WWW pages, based on the data retrieved by the file retrieving unit 3222. Thus, the display data creating unit 3223 functions as a WWW page creator.

When a product to be purchased (such as a contact lens) is selected via the mobile interface 3001, the contact lens ordering and marketing processor 3023 receives a user ID and a product ID to be purchased from the display information creating unit 3022. Based on this information, the processing unit 3023 then obtains detailed information about the product to be purchased from the product database, and stores the product information in a user basket database corresponding to the user within the basket database. Subsequently, the contact lens ordering and marketing processing unit 3023 obtains a list of products to be purchased by the purchaser from the basket database, and then passes the list to the display information creating unit 3022.

The lens selection unit 3026 selects or determines a contact lens from among a plurality of contact lenses in response to the requests sent from the purchaser via the mobile interface 3001, sends information regarding the ordering and marketing to the mobile interface 3001, so as to enter into a contact lens sales contract with the purchaser.

When the purchase of the product is confirmed by the mobile interface 3001, the settling unit 3024 receives the user ID from the display information creating unit 3022 to retrieve product data information corresponding to the purchaser from the basket database. Then, based on the product data information that has been retrieved, the settling unit 3024 makes a request to the external settling institution 3003 for settling processing. The settling unit 3024 is informed of the completion of the settling processing by the external settling institution 3003, and thereafter notifies the contact lens ordering and marketing processor 3023 and the electronic shop information processor 3021 that an order acceptance processing has been completed. In order to notify the mobile interface 3001 of the purchase processing, the settling unit 3024 also prepares invoice data, on which to base the process, to send the invoice data to the display information creating unit 3022.

The WWW server/CGI 3025 defines an interface to the mobile interface 3001 to receive display request information from the mobile interface 3001 as well as transfer display data to the mobile interface 3001.

Based on the request sent from the settling unit 3024 of the contact lens ordering and marketing service center 3002, the external settling institution 3003 performs a settling processing task for payment of the ordered contact lens.

Now, the outline of the operation of the mobile interface 3001 and the contact lens ordering and marketing service center 3002 will be described below.

In the contact lens ordering and marketing service center 3002, the WWW server/CGI 3025 receives contact lens ordering page information that is sent from the mobile interface 3001, and then activates the display information creating unit 3022 under the control of the controlling unit 3030.

The display information creating unit 3022 is activated to receive the contact lens ordering page information from the WWW server/CGI 3025, which then permits the parameter analysis unit 3221 to analyze the information.

The parameter analysis unit 3221 outputs information as analytical results such as a shop ID for identifying an electronic shop to be displayed, a catalog template for determining the type of a background image for an electronic catalog, the product ID of a product to be displayed, and a user ID for identifying the purchaser.

Based on the data output from the parameter analysis unit 3221, the file retrieving unit 3222 retrieves data in the shop database, product database, and basket database, the data being necessary for creating a display window of a homepage requested by the mobile interface 3001 for display.

After the file retrieving unit 3222 has retrieved the data, the process is transferred to the display data creating unit 3223.

The display data creating unit 3223 first identifies the type of a request from the mobile interface 3001. When the request from the mobile interface 3001 is one other than "the determination of a product to be purchased" and "the purchase of a product," the display data creating unit 3223 creates data for display using the result retrieved by the file retrieving unit 3222.

Suppose that the type of request from the mobile interface 3001 has been identified as "the determination of a product to be purchased" in the step of identifying the type of a request from the mobile interface 3001. That is, when the user has provided an instruction of "putting a selected product into a shopping basket" to instruct to reserve a product being displayed, the display data creating unit 3223 activates the contact lens ordering and marketing processor 3023.

The contact lens ordering and marketing processor 3023 is activated to receive a user ID and the product ID of the product, which the user has instructed to purchase, from the display data creating unit 3223. With this product ID as key information, the processor 3023 receives detailed product data information about the corresponding product from the product database.

Then, the product data information retrieved in the foregoing step is stored in the user basket database of the user within the basket database, the user being identified by the user ID received from the display data creating unit 3223. At this point, when no corresponding user basket database exists, a user basket database that corresponds to the user ID is created to store the product data information therein.

Then, all pieces of the product data information of the products that the user has selected are retrieved from the user basket database and passed to the display data creating unit 3223. In this case, the display data creating unit 3223 creates a list of display information on the products that the user intends to purchase, based on the product data information received from the contact lens ordering and marketing processor 3023, and then sends the list of display information to the mobile interface 3001. Based on the information displayed, the user can check the products to be purchased or cancel part or all of the products to be purchased.

Suppose that the type of request from the mobile interface 3001 has been identified as "the purchase of a product" in the step of identifying the type of a request from the mobile interface 3001. In other words, when the user has provided an instruction of his/her decision concerning the purchase of the products that the user has selected, the display data creating unit 3223 activates the settling unit 3024 prior to the creation of display data.

The settling unit 3024 is activated to receive a user ID from the display data creating unit 3223. With the received user ID, the settling unit 3024 retrieves the product data information of the purchased product in the user basket database of the user identified with the user ID in the basket database. Based on the resulting product data information, a request for settling processing is sent to the external settling institution 3003.

In response to the request, the external settling institution 3003 performs a settling processing task, and then notifies the contact lens ordering and marketing service center 3002 of the completion of the settling processing when completed. Since the settling processing performed in the external settling institution 3003 is conventional, no detailed description is provided for the settling processing herein.

Upon receipt of a notification from the external settling institution 3003 that the settling processing has been completed, the settling unit 3024 forwards the order information that has been received to the contact lens ordering and marketing service center 3002. The information about the order received includes information about the ordered product such as the product number and quantity of the product, information about the destination of the product, and the settling information such as the name of the external settling institution 3003 and the date and amount of payment. In the contact lens ordering and marketing service center 3002, the information about the order received from the WWW server/ CGI 3025 via an I/O unit is displayed.

Then, the settling unit 3024 creates invoice data for notifying of the completion of the settling processing and transmits the invoice data to the display data creating unit 3223.

The display data creating unit 3223 uses the invoice data that has been received to create a display window for notifying of the completion of the settling processing, and thus, forwards the window to the mobile interface 3001.

Next, the method of ordering and marketing contact lenses via the network-based contact lens ordering and marketing system will be described below with reference to FIG. 31 to FIG. 52.

This method offers a contact lens delivery service whereby customers who have bought a disposable contact lens within one year before the application date for the delivery service can order the same contact lens as the one currently in use via a mobile interface 3001.

This system, therefore, is not designed for sales to people who have no purchase history of contact lenses for more than one year. Also, the system does not accept an order for a different contact lens from the one bought before. It only allows for ordering of the same contact lens as the previously purchased one.

This is to prevent contact lens wearers from purchasing a contact lens in accordance with an outdated prescription for health reasons.

Those who have bought a contact lens are given the chance of applying for the contact lens delivery service with an application form shown in FIG. 32 upon agreeing to its terms of use.

The applicants are requested to fill in the application form including their names, addresses, phone numbers, i-mode or e-mail addresses, IDs, passwords, places of delivery of products, and payment methods including credit card information such as card numbers, types, and expiration dates. The registration information specified in these application forms is input with an input device, recorded and stored in a WEB data file 3027 at the contact lens ordering and marketing service center 3002.

The service center keeps another registered user data file (host data) 3028 in which is recorded and managed data regarding the customers who have bought contact lenses within the past one year, including basic information such as addresses, names, and phone numbers, as well as data regarding magnification number or other useful information about the contact lenses that they are now wearing. The WEB data file (WEB data) 3027 is compared with the registered user data file (host data) 3028, and if the latter contains data on the user who has applied for the registration this time, the WEB data file (WEB data) 3027 is confirmed and managed to register this user as a prospective purchaser of contact lenses (S301).

Figure 33:
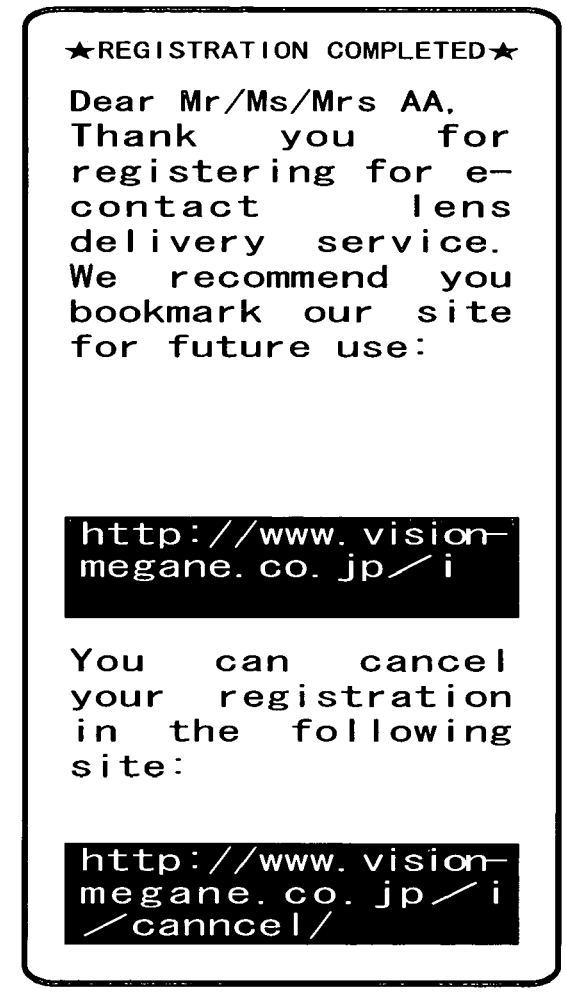
FIG. 33 is a diagrammatic view illustrating an e-mail confirming the completion of registration for a contact lens delivery service.

Next, when data registration of the applicant for the contact lens delivery service is completed as a WEB data file, a message shown in FIG. 33 is sent to the user notifying him or her of the completion of registration. At this time, a follow-up confirmation message is also sent to ask the user to check whether there are any mistakes in the application form or input errors at the contact lens ordering and marketing service center 3002 of the registration information on the user.

The first time the user uses the delivery service, the user is asked to register (S302).

Figure 34:
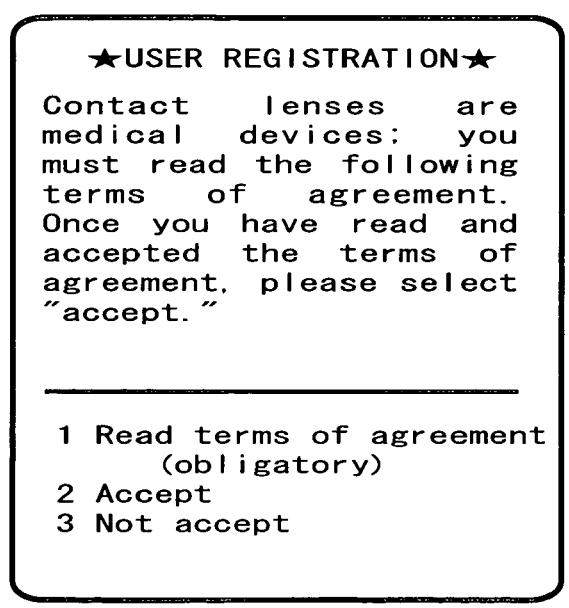
FIG. 34 is a diagrammatic view illustrating a screen displaying "user registration."

That is, the controller 3030 controls the display information creating unit 3022 and lens ordering and marketing processor 3023 to transmit a "user registration" window shown in FIG. 34 to the mobile interface 3001.

The "user registration" window prompts the user to read the terms of agreement. When the user selects "read the terms of agreement (obligatory)," the "terms of agreement" windows shown in FIGS. 35 and 36 are transmitted. The "terms of agreement" windows ask the user to accept and comply with the terms of use for the contact lens delivery service, prompting the user to select "accept" in the window if the user has read and agreed to accept the terms (S303).

Figure 37:
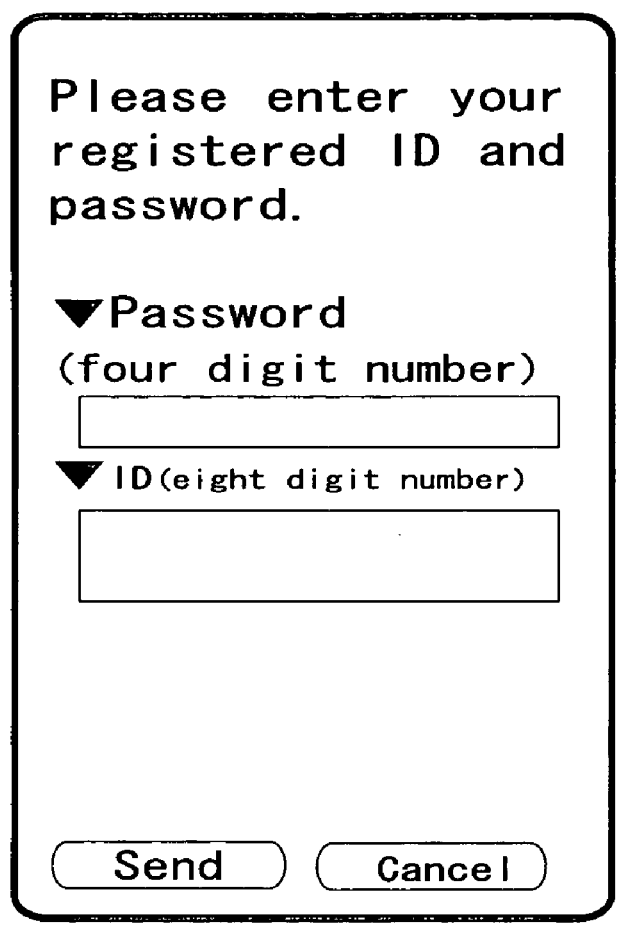
FIG. 37 is a diagrammatic view illustrating a screen for identification of a user.

In response to the user's selection of "accept" from the mobile interface 3001, the controller 3030 at the contact lens ordering and marketing service center 3002 controls the display information creating unit 3022 and lens ordering and marketing processor 3023 to transmit a user authentication window shown in FIG. 37 to the mobile interface 3001.

Thereupon, the user inputs his or her password and ID in the "user authentication" window that appears on the screen of the mobile interface 3001 (S304).

The contact lens ordering and marketing service center 3002 performs authentication by comparing the password and ID sent from the mobile interface 3001 with data in the WEB data file 3027, in which is previously registered and controlled the information on registered users of the delivery service (S305).

Figure 38:
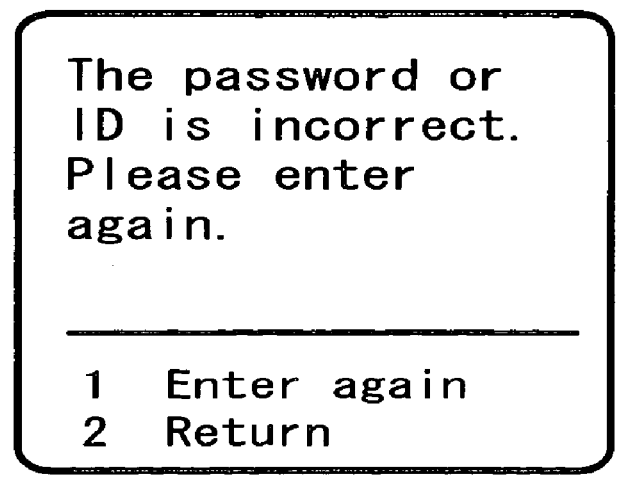
FIG. 38 is a diagrammatic view illustrating a screen for identification of a user for re-identifying a user.

When the user authentication fails, the controller 3030 executes control to transmit another user authentication window shown in FIG. 38 from the contact lens ordering and marketing service center 3002.

If the user is authenticated and identified as a customer who visited the shop more than one year before that date, a "notice" window shown in FIG. 39 is transmitted to the mobile interface 3001 from the contact lens ordering and marketing service center 3002, reminding the user that it has been more than a year and suggesting that the user visits an ophthalmologist to test the vision again and get a new prescription (S306).

If the user's credit card has expired, a "notice" window shown in FIG. 39 is transmitted to the mobile interface 3001 from the contact lens ordering and marketing service center 3002, notifying the user of this fact and prompting the user to inform the service center 3002 of a new expiration date (S307).

If the user has visited the shop within the past year, the controller 3030 at the contact lens ordering and marketing service center 3002 controls the display information creating unit 3022 and lens ordering and marketing processor 3023 to transmit a "registration procedure completed" window shown in FIG. 40 containing a message that now the user can place an order.

Thereupon the contact lens delivery service is commenced.

If there is an error in inputting the password or ID, the controller 3030 controls the display information creating unit 3022 and lens ordering and marketing processor 3023 to transmit a window shown in FIG. 38 notifying the user of the input error in the password or ID from the contact lens ordering and marketing service center 3002 to the mobile interface 3001.

If the user is not a registered member of the service, the controller 3030 controls the display information creating unit 3022 and lens ordering and marketing processor 3023 to transmit a window shown in FIG. 41 from the service center 3002 to the mobile interface 3001 informing the user of the fact that he or she was not found in the member list.

If the user has visited the shop within the past one year and gone through the registration procedure, the "registration procedure completed" window shown in FIG. 40 containing a message that prompts the user to place an order is transmitted. If the user selects "repeat of previous order" in the "registration procedure completed" window in the mobile interface 3001, the controller 3030 at the contact lens ordering and marketing service center 3002 controls the display information creating unit 3022 and lens selection unit 3026 to transmit an "condition confirmation" window shown in FIG. 42 to the mobile interface 3001, indicating the conditions of the contact lenses currently in use (S308).

The user at the mobile interface 3001 who receives this "condition confirmation" window confirms whether or not the specifications of the contact lenses meet the user's needs (S309), and checks the contents of purchase conditions or the like (S310).

The user will select "yes" in the "condition confirmation" window if all the information is correct.

When this affirmative answer is received by the contact lens ordering and marketing service center 3002, the controller 3030 executes control of the display information creating unit 3022 and lens ordering and marketing processor 3023 to transmit a "delivery location selection" window shown in FIG. 43. The user selects "OK" in this window sent from the contact lens ordering and marketing service center 3002 if it shows a correct delivery location. If the user wishes to select a different delivery location from the registered one, the user will select "change" in the "delivery location selection" window (S311). In response to this, the controller 3030 at the contact lens ordering and marketing service center 3002 controls the display information creating unit 3022 and lens ordering and marketing processor 3023 to transmit an input window shown in FIG. 44 that permits a different address to be entered.

When the new address is confirmed, the controller 3030 at the contact lens ordering and marketing service center 3002 controls the lens selection unit 3026 to transmit a "lens selection" window shown in FIG. 45 to the mobile interface 3001 such that the user can select a lens that user wants to order (S312).

Next, the contact lens ordering and marketing service center 3002 transmits a "determination of number of order items" window shown in FIG. 46 to the mobile interface 3001 for allowing a number of order items to be determined, by the control executed by the controller 3030 of the display information creating unit 3022 and lens ordering and marketing processor 3023 (S313).

After the type of lens to be ordered is selected in the "lens selection" window (FIG. 45) and the number of lenses is determined in the "determination of number of order items" window (FIG. 46), the payment method for the price of the contact lenses is confirmed (S314).

At the contact lens ordering and marketing service center 3002, the controller 3030 controls the settling unit 3024 to transmit a payment method confirmation window shown in FIG. 47 to the mobile interface 3001.

The "payment method confirmation" window allows the user to select from three options—credit card, cash on delivery, or pay in shop.

After completing the above confirmation, the controller 3030 at the contact lens ordering and marketing service center 3002 controls the display information creating unit 3022 and lens ordering and marketing processor 3023 to transmit a window that allows the user to confirm the price and contents of order (FIG. 48) to the mobile interface 3001 (S315). This confirmation window shows the number and type of ordered lenses, lens data, delivery location, addressee, phone number, payment method, product price, shipping charges, and others.

The user checks the "order price and contents confirmation" window sent to the mobile interface 3001, and if the information given in that window corresponds to the user's intentions, the user selects "order", but if there is a mistake, the user can select "cancel" to cancel the order.

When "order" is selected, the contact lens ordering and marketing service center 3002 transmits a delivery date confirmation window shown in FIG. 49 to the mobile interface 3001.

Thereupon, at the contact lens ordering and marketing service center 3002, the controller 3030 controls the electronic shop information processor 3021 to check whether the lenses are in stock. It then controls the display information creating unit 3022 and lens ordering and marketing processor 3023 to indicate the order date and delivery location of the ordered item, and to transmit the confirmation window (FIG. 49) indicating the order contents, ordered lenses, lens data, place of delivery, addressee, phone number, payment method, price of products, and shipping charges to the mobile interface 3001.

As mentioned above, if the user is identified as a registered member who has visited the shop within the past one year, the user receives the "registration procedure completed" window (FIG. 40) containing a message that prompts the user to place an order. If the "repeat of previous order" is selected in the "registration procedure completed" window in the mobile interface 3001, the controller 3030 at the contact lens ordering and marketing service center 3002 controls the display information creating unit 3022 and lens selection unit 3026 to transmit the "condition confirmation" window (FIG. 42) indicating the conditions of the contact lenses currently in use to the mobile interface 3001. If the user checks the "condition confirmation" window and finds it contrary to the user's intentions, the user selects "No" in this window in the mobile interface 3001.

When the contact lens ordering and marketing service center 3002 receives this negative answer, the controller 3030 controls the display information creating unit 3022 and lens ordering and marketing processor 3023 to transmit a window (FIG. 50) to the mobile interface 3001, prompting the user to input correct specifications (S316).

Figure 52:
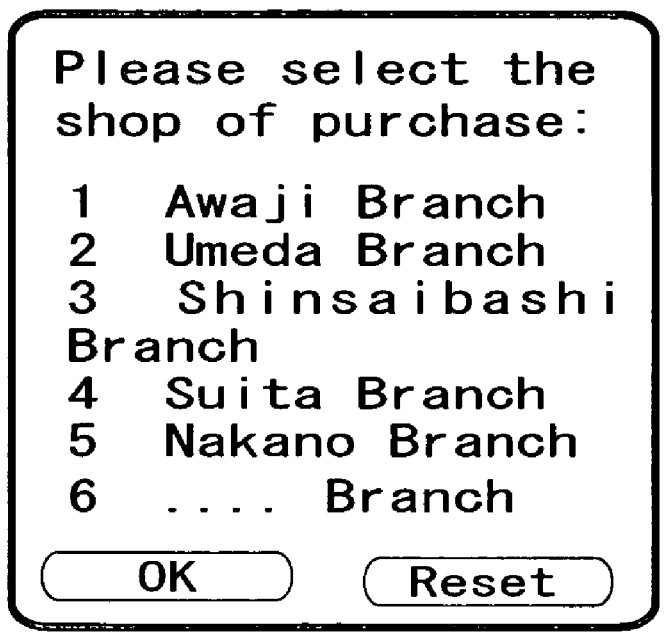
FIG. 52 is a diagrammatic view illustrating a second screen for selecting a shop of purchase.

Next, the controller 3030 at the contact lens ordering and marketing service center 3002 controls the display information creating unit 3022 and lens ordering and marketing processor 3023 to transmit windows shown in FIG. 51 and FIG. 52 for selecting a shop of purchase to the mobile interface 3001 (S317).

Figure 53:
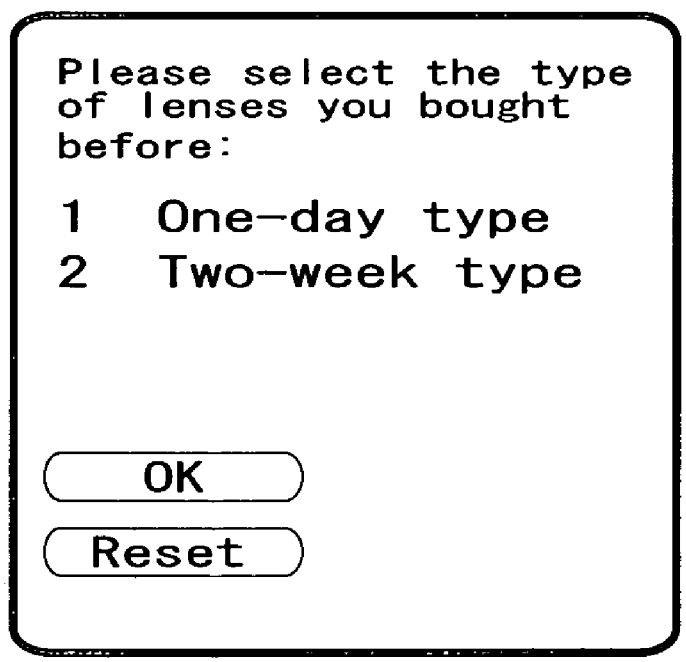
FIG. 53 is a diagrammatic view illustrating a screen for selecting a type of contact lens that a user bought before.

Successively, a window (FIG. 53) for selecting a lens that has previously been purchased is transmitted to the mobile interface 3001 by the display information creating unit 3022 and lens ordering and marketing processor 3023.

When the purchased lens is selected, the above described service is provided to the user.

If the contact lens ordering and marketing service center 3002 determines that there is a mistake in the transmitted data, it decides that there has been an error and informs the user thereof via e-mail.

As described above, according to the present invention, eyeglasses with specifications that corresponds to the vision and other requirements of each user can be ordered and marketed remotely by making use of a network.

It should be understood that the foregoing description is only illustrative of the present invention. Various alternatives and modifications can be devised by those skilled in the art without departing from the present invention. Accordingly, the present invention is intended to embrace all such alternatives, modifications and variances which fall within the scope of the appended claims.

The invention claimed is:

1. A method for ordering and marketing eyeglasses via a network using a user interface unit or a mobile interface, an eyeglass ordering and marketing service center, and a network connecting therebetween, the method comprising:

retrieving vision test data and sending an inquiry window to the user interface unit or the mobile interface to check whether new eyeglasses may be made according to previous data of a purchaser that is a registered user, based on the vision test data, which are controlled in the user database including basic attributes which are input by the user via a basic attribute input window, the basic attributes in the user database include whether or not the purchaser is a registered user;

sending an inquiry window to the user interface unit or the mobile interface for checking if a purchaser has a doctor's prescription, when it is determined that the purchaser is not a registered user by retrieving the user database;

sending an inquiry window to the user interface unit or the mobile interface for checking if the purchaser is over 40 years of age, if the purchaser does not have a doctor's prescription;

sending an inquiry window to the user interface unit or the mobile interface for checking if the purchaser has difficulty in viewing near distances, and sending an inquiry window to the user interface unit or the mobile interface for checking if the purchaser desires to order presbyopic eyeglasses, in case the purchaser inputs that the purchaser is aware of difficulty in viewing near distances;

selecting an eyeglass frame from among a plurality of eyeglass frames for a user;

creating display information related to eyeglass frames;

testing vision of the user;

selecting an eyeglass lens from among a plurality of eyeglass lenses for the user;

prompting the users who are over 40 years of age to select either presbyopic or bifocal lenses, by judging from the viewpoint of age;

processing eyeglass ordering and marketing made based on said eyeglass frame selection step, said vision test step and said lens selection step, such that vision is tested and eyeglass frames and lenses suitable therefor are determined, in response to a requirement of the user sent from the user interface unit or the mobile interface, providing the user interface unit or the mobile interface with information relating to ordering and marketing, and concluding an eyeglass purchase contract with the user; and creating display information relating to eyeglass frames in cooperation with or independently of said frame selection step or said eyeglass ordering and marketing processing step, and for transmitting the information on the eyeglass frames to the user interface unit or the mobile interface.

2. A network-based eyeglass ordering and marketing system comprising a user interface unit or a mobile interface, an eyeglass ordering and marketing service center, and a network connecting therebetween, wherein said network-based eyeglass ordering and marketing systems further comprises:

a unit for retrieving vision test data and sending an inquiry window to the user interface unit or the mobile interface to check whether new eyeglasses may be made according to previous data of a purchaser that is a registered user, based on the vision test data, which are controlled in a user database including basic attributes which are input by the user via a basic attribute input window, the basic attributes in the user database include whether or not the Purchaser is a registered user;

a unit for sending an inquiry window to the user interface unit or the mobile interface for checking if the purchaser has a doctor's prescription, when it is determined that the purchaser is not a registered user by retrieving the user database;

a unit for sending an inquiry window to the user interface unit or the mobile interface for checking if the purchaser is over 40 years of age, if the purchaser does not have a doctor's prescription;

a unit for sending an inquiry window to the user interface unit or the mobile interface for checking if the Purchaser has difficulty in viewing near distances, and a unit for sending an inquiry window to the user interface unit or the mobile interface for checking if the purchaser inputs that the purchaser desires to order presbyopic eyeglasses, in case the purchaser input that the purchaser is aware of difficulty in viewing near distances;

a frame selection unit for selecting an eyeglass frame from among a plurality of eyeglass frames for a user;

a unit for creating display information related to eyeglass frames;

a unit for testing vision of the user;

a lens selection unit for selecting an eyeglass lens from among a plurality of eyeglass lenses for the user;

an eyeglasses selection unit for prompting the users who are over 40 years of age, to select either presbyopic or bifocal lenses;

an eyeglass ordering and marketing processing unit for enabling said frame selection unit, said vision testing unit and said lens selection unit, to test vision and to determine eyeglass frames and lenses suitable for the user, in response to a requirement of the user sent from the user interface unit or the mobile interface, for providing the user interface unit or the mobile interface with information relating to ordering and marketing, and for concluding an eyeglass purchase contract with the user; and a display information creating unit for creating information relating to eyeglass frames in cooperation with or independently of said frame selection unit or said eyeglass ordering and marketing processing unit, and for transmitting the information related to the eyeglass frames to the user interface unit or the mobile interface.

3. A program embodied on a recording medium of a network-based eyeglass ordering and marketing system recorded thereon, the system comprising a user interface unit or a mobile interface, an eyeglass ordering and marketing service center, and a network connecting therebetween, wherein the program embodied on the recording medium of the network-based eyeglass ordering and marketing system comprises:

a unit for retrieving vision test data and sending an inquiry window to the user interface unit or the mobile interface to check whether new eyeglasses may be made according to previous data of a purchaser that is a registered user, based on the vision test data, which are controlled in a user database including basic attributes which are input by the user via a basic attribute input window, the basic attributes in the user database include whether or not the purchaser is a registered user;

a unit for sending an inquiry window to the user interface unit or the mobile interface for checking if the purchaser has a doctor's prescription, when it is determined that the purchaser is not a registered user by retrieving the user database;

a unit for sending an inquiry window to the user interface unit or the mobile interface for checking if the purchaser is over 40 years of age, if the purchaser does not have a doctor's prescription;

a unit for sending an inquiry window to the user interface unit or the mobile interface for checking if the purchaser has difficulty in viewing near distances, and a unit for sending an inquiry window to the user interface unit or the mobile interface for checking if the purchaser inputs that the purchaser desires to order presbyopic eyeglasses, in case the purchaser input that the purchaser is aware of difficulty in viewing near distances;

a frame selection unit for selecting an eyeglass frame from among a plurality of eyeglass frames for a user;

a unit for creating display information related to eyeglass frames;

a unit for testing vision of the user;

a lens selection unit for selecting an eyeglass lens from among a plurality of eyeglass lenses for the user;

an eyeglasses selection unit for prompting the users who are over 40 years of age, to select either presbyopic or bifocal lenses;

an eyeglass ordering and marketing processing unit for enabling said frame selection unit, said vision testing unit and said lens selection unit, to test vision and to determine eyeglass frames and lenses suitable for the user, in response to a requirement of the user sent from the user interface unit or the mobile interface, for providing the user interface unit or the mobile interface with information relating to ordering and marketing, and for concluding an eyeglass purchase contract with the user; and a display information creating unit for creating information relating to eyeglass frames in cooperation with or independently of said frame selection unit or said eyeglass ordering and marketing processing unit, and for transmitting the information related to the eyeglass frames to the user interface unit or the mobile interface.

4. A program embodied on a computer readable medium and executable by a computer or processor for executing a method of ordering and marketing eyeglasses via a network using a user interface unit or a mobile interface, an eyeglass ordering and marketing service center, and a network connecting therebetween, the program comprising the steps of:

retrieving vision test data and sending an inquiry window to the user interface unit or the mobile interface to check whether new eyeglasses may be made according to previous data of a purchaser that is a registered user, based on the vision test data, which are controlled in the user database including basic attributes which are input by the user via a basic attribute input window, the basic attributes in the user database include whether or not the purchaser is a registered user;

sending an inquiry window to the user interface unit or the mobile interface for checking if a purchaser has a doctor's prescription, when it is determined that the purchaser is not a registered user by retrieving the user database;

sending an inquiry window to the user interface unit or the mobile interface for checking if the purchaser is over 40 years of age, if the purchaser does not have a doctor's prescription;

sending an inquiry window to the user interface unit or the mobile interface for checking if the purchaser has difficulty in viewing near distances, and sending an inquiry window to the user interface unit or the mobile interface for checking if the purchaser desires to order presbyopic eyeglasses, in case the purchaser inputs that the purchaser is aware of difficulty in viewing near distances;

selecting an eyeglass frame from among a plurality of eyeglass frames for a user;

creating display information related to eyeglass frames;
testing vision of the user;
selecting an eyeglass lens from among a plurality of eyeglass lenses for the user;
prompting the users who are over 40 years of age to select either presbyopic or bifocal lenses, by judging from the viewpoint of age;
processing eyeglass ordering and marketing made based on said eyeglass frame selection step, said vision test step and said lens selection step, such that vision is tested and eyeglass frames and lenses suitable therefor are determined, in response to a requirement of the user sent from the user interface unit or the mobile interface, providing the user interface unit or the mobile interface with information relating to ordering and marketing, and concluding an eyeglass purchase contract with the user; and
creating display information relating to eyeglass frames in cooperation with or independently of said frame selection step or said eyeglass ordering processing step, and for transmitting the information on the eyeglass frames to the user interface unit or the mobile interface.

* * * * *